United States Patent
de Mollerat du Jeu et al.

(10) Patent No.: US 10,792,362 B2
(45) Date of Patent: *Oct. 6, 2020

(54) COMPOSITIONS AND METHODS FOR EFFICIENT DELIVERY OF MOLECULES TO CELLS

(71) Applicant: LIFE TECHNOLOGIES CORPORATION, Carlsbad, CA (US)

(72) Inventors: Xavier de Mollerat du Jeu, Encinitas, CA (US); Nektaria Andronikou, Vista, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,393

(22) Filed: Dec. 21, 2018

(65) Prior Publication Data

US 2019/0201530 A1    Jul. 4, 2019

Related U.S. Application Data

(63) Continuation of application No. 14/800,565, filed on Jul. 15, 2015, now Pat. No. 10,195,280.

(60) Provisional application No. 62/024,918, filed on Jul. 15, 2014.

(51) Int. Cl.
| | |
|---|---|
| A61K 47/18 | (2017.01) |
| A61K 9/127 | (2006.01) |
| A61K 31/7105 | (2006.01) |
| C12N 15/88 | (2006.01) |

(52) U.S. Cl.
CPC .......... A61K 47/186 (2013.01); A61K 9/1272 (2013.01); A61K 31/7105 (2013.01); C12N 15/88 (2013.01)

(58) Field of Classification Search
None
See application file for complete search history.

(56) References Cited

U.S. PATENT DOCUMENTS

| | | | |
|---|---|---|---|
| 2,046,720 A | 7/1936 | Bottoms | |
| 2,654,785 A | 10/1953 | Miescher et al. | |
| 2,695,314 A | 11/1954 | Kusmln | |
| 2,867,665 A | 1/1959 | Dornfeld | |
| 2,901,461 A | 8/1959 | Auerbach et al. | |
| 2,933,529 A | 4/1960 | Jesse | |
| 3,152,188 A | 10/1964 | Kirkpatrick et al. | |
| 3,324,182 A | 6/1967 | DeBrunner et al. | |
| 3,369,905 A | 2/1968 | Jones et al. | |
| 4,143,003 A | 3/1979 | Haas et al. | |
| 4,235,871 A | 11/1980 | Papahadjopoulos et al. | |
| 4,501,728 A | 2/1985 | Geho et al. | |
| 4,625,064 A | 11/1986 | Kumoi et al. | |
| 4,683,195 A | 7/1987 | Mullis et al. | |
| 4,683,202 A | 7/1987 | Mullis | |
| 4,737,323 A | 4/1988 | Martin et al. | |
| 4,767,699 A | 8/1988 | Vary et al. | |
| 4,800,159 A | 1/1989 | Mullis et al. | |
| 4,812,449 A | 3/1989 | Rideout | |
| 4,837,028 A | 6/1989 | Allen | |
| 4,889,818 A | 12/1989 | Gelfand et al. | |
| 4,889,953 A | 12/1989 | Inoue et al. | |
| 4,897,355 A | 1/1990 | Eppstein et al. | |
| 4,946,787 A | 8/1990 | Eppstein et al. | |
| 4,959,217 A | 9/1990 | Sanders et al. | |
| 4,962,022 A | 10/1990 | Fleming et al. | |
| 4,965,188 A | 10/1990 | Mullis et al. | |
| 4,967,008 A | 10/1990 | Friedli et al. | |
| 5,047,342 A | 9/1991 | Chatterjee | |
| 5,049,386 A | 9/1991 | Eppstein et al. | |
| 5,079,352 A | 1/1992 | Gelfand et al. | |
| 5,091,576 A | 2/1992 | Bergeron | |
| 5,165,925 A | 11/1992 | Leong | |
| 5,166,320 A | 11/1992 | Wu et al. | |
| 5,171,678 A | 12/1992 | Behr et al. | |
| 5,186,923 A | 2/1993 | Piwnica-Worms et al. | |
| 5,187,085 A | 2/1993 | Lee | |
| 5,196,135 A | 3/1993 | Merianos | |

(Continued)

FOREIGN PATENT DOCUMENTS

| | | |
|---|---|---|
| AU | 2652692 | 5/1993 |
| AU | 158967 | 10/1997 |

(Continued)

OTHER PUBLICATIONS

US 7,189,874 B2, 03/2007, Chu et al. (withdrawn)
10153820.5, "Extended European Search report dated Dec. 28, 2010", 11 pages.
Ahmed, O.A. et al., "N4,N9-dioleoyl spermine is a novel nonviral lipopolyamine vector for plasmid DNA formulation", *Pharmaceutical Research*, vol. 22, No. 6, Jun. 8, 2005, pp. 972-980.
Ahmed, O.A. et al., "Varying the Unsaturation in N4,N9-Dioctadecanoyl Spermines: Nonviral Lipopolyamine Vectors for More Efficient Plasmid DNA Formulation", *Pharmaceutical Research*, vol. 23, No. 1, Jan. 2006, pp. 31-40.
Albrecht, T. et al., "Cationic lipide mediated transfer of c-abl and bcr antisense oligonucleotides to immature normal myeloid cells: Uptake, biological effects and modulation of gene expression", *Annals of Hematology*, vol. 72, Springer-Verlag, 1996, 73-79.

(Continued)

*Primary Examiner* — Michael D Burkhart
(74) *Attorney, Agent, or Firm* — Life Technologies Corporation; Karen R. Zachow

(57) ABSTRACT

The present invention provides lipid aggregate compositions having at least two cationic lipids in combination with one or optionally more than one non-cationic lipids for the in vitro and/or in vivo delivery of biologically active molecules including nucleic acids, specifically DNA and RNA, and proteins into cells and tissues. Methods are also provided that use the compounds of the present invention to deliver biologically active molecules, into cells and tissues to facilitate the expression of target proteins therein. In some non-limiting embodiments, the subject lipid aggregate compositions can be used to deliver nucleic acid molecules to facilitate the expression of proteins involved in cellular reprogramming and genome editing applications.

43 Claims, 2 Drawing Sheets

(56) References Cited

U.S. PATENT DOCUMENTS

| | | |
|---|---|---|
| 5,198,423 A | 3/1993 | Taguchi et al. |
| 5,208,036 A | 5/1993 | Eppstein et al. |
| 5,242,684 A | 9/1993 | Merianos |
| 5,244,797 A | 9/1993 | Kotewicz et al. |
| 5,264,423 A | 11/1993 | Cohen et al. |
| 5,264,618 A | 11/1993 | Felgner et al. |
| 5,266,106 A | 11/1993 | Breton |
| 5,270,179 A | 12/1993 | Chatterjee |
| 5,276,019 A | 1/1994 | Cohen et al. |
| 5,277,897 A | 1/1994 | Piwnica-Worms et al. |
| 5,279,833 A | 1/1994 | Rose |
| 5,283,185 A | 2/1994 | Epand et al. |
| 5,286,717 A | 2/1994 | Cohen et al. |
| 5,328,470 A | 7/1994 | Nabel et al. |
| 5,328,984 A | 7/1994 | Pastan et al. |
| 5,334,761 A | 8/1994 | Gebeyehu et al. |
| 5,338,532 A | 8/1994 | Tomalia et al. |
| 5,350,672 A | 9/1994 | Oberst et al. |
| 5,354,844 A | 10/1994 | Beug et al. |
| 5,374,553 A | 12/1994 | Gelfand et al. |
| 5,401,084 A | 3/1995 | Volz et al. |
| 5,409,818 A | 4/1995 | Davey et al. |
| 5,436,149 A | 7/1995 | Barnes |
| 5,455,166 A | 10/1995 | Walker |
| 5,455,335 A | 10/1995 | Kahne et al. |
| 5,459,127 A | 10/1995 | Felgner et al. |
| 5,484,702 A | 1/1996 | Ludwig |
| 5,498,522 A | 3/1996 | Porter |
| 5,498,523 A | 3/1996 | Tabor et al. |
| 5,500,356 A | 3/1996 | Li et al. |
| 5,506,212 A | 4/1996 | Hoke et al. |
| 5,510,239 A | 4/1996 | Baracchini, Jr. et al. |
| 5,510,476 A | 4/1996 | Ravikumar et al. |
| 5,512,438 A | 4/1996 | Ecker |
| 5,512,462 A | 4/1996 | Cheng |
| 5,514,577 A | 5/1996 | Draper et al. |
| 5,514,787 A | 5/1996 | Arkinson |
| 5,519,134 A | 5/1996 | Acevedo et al. |
| 5,521,291 A | 5/1996 | Curiel et al. |
| 5,521,302 A | 5/1996 | Cook |
| 5,527,524 A | 6/1996 | Tomalia et al. |
| 5,527,928 A | 6/1996 | Nantz et al. |
| 5,532,142 A | 7/1996 | Johnston et al. |
| 5,541,307 A | 7/1996 | Cook et al. |
| 5,543,507 A | 8/1996 | Cook et al. |
| 5,545,412 A | 8/1996 | Eppstein et al. |
| 5,545,540 A | 8/1996 | Mian |
| 5,547,932 A | 8/1996 | Curiel et al. |
| 5,550,289 A | 8/1996 | Eppstein et al. |
| 5,554,746 A | 9/1996 | Ravikumar et al. |
| 5,560,929 A | 10/1996 | Hedstrand et al. |
| 5,574,142 A | 11/1996 | Meyer et al. |
| 5,578,475 A | 11/1996 | Jessee |
| 5,580,859 A | 12/1996 | Felgner et al. |
| 5,583,198 A | 12/1996 | Whittaker |
| 5,587,441 A | 12/1996 | Frechet et al. |
| 5,587,446 A | 12/1996 | Frechet et al. |
| 5,588,718 A | 12/1996 | Winner et al. |
| 5,589,392 A | 12/1996 | Short |
| 5,589,466 A | 12/1996 | Felgner et al. |
| 5,595,096 A | 1/1997 | Coffman |
| 5,595,897 A | 1/1997 | Midoux et al. |
| 5,596,091 A | 1/1997 | Switzer |
| 5,602,240 A | 2/1997 | De Mesmaeker et al. |
| 5,614,365 A | 3/1997 | Tabor et al. |
| 5,621,730 A | 4/1997 | Kelley et al. |
| 5,627,159 A | 5/1997 | Shih et al. |
| 5,631,329 A | 5/1997 | Yin et al. |
| 5,635,487 A | 6/1997 | Wolff et al. |
| 5,641,662 A | 6/1997 | Debs et al. |
| 5,650,096 A | 7/1997 | Harris et al. |
| 5,658,776 A | 8/1997 | Flotte et al. |
| 5,661,025 A | 8/1997 | Szoka et al. |
| 5,667,774 A | 9/1997 | Figuly |
| 5,670,347 A | 9/1997 | Gopal |
| 5,674,908 A | 10/1997 | Haces et al. |
| 5,676,954 A | 10/1997 | Brigham |
| 5,681,944 A | 10/1997 | Crooke et al. |
| 5,691,460 A | 11/1997 | Duvic et al. |
| 5,693,509 A | 12/1997 | Cotten et al. |
| 5,693,773 A | 12/1997 | Kandimalla et al. |
| 5,703,055 A | 12/1997 | Felgner et al. |
| 5,705,385 A | 1/1998 | Bally et al. |
| 5,714,166 A | 2/1998 | Tomalia et al. |
| 5,719,131 A | 2/1998 | Harris et al. |
| 5,726,298 A | 3/1998 | Hirai et al. |
| 5,736,387 A | 4/1998 | Paul et al. |
| 5,736,392 A | 4/1998 | Hawley-Nelson et al. |
| 5,744,335 A | 4/1998 | Wolff et al. |
| 5,744,625 A | 4/1998 | Nantz et al. |
| 5,753,613 A | 5/1998 | Ansell et al. |
| 5,756,353 A | 5/1998 | Debs |
| 5,759,778 A | 6/1998 | Li et al. |
| 5,759,805 A | 6/1998 | Feldhaus et al. |
| 5,773,527 A | 6/1998 | Tomalia et al. |
| 5,780,053 A | 7/1998 | Ashley et al. |
| 5,783,565 A | 7/1998 | Lee et al. |
| 5,783,566 A | 7/1998 | Mislick |
| 5,785,992 A | 7/1998 | Ansell et al. |
| 5,795,587 A | 8/1998 | Gao et al. |
| 5,807,746 A | 9/1998 | Lin et al. |
| 5,824,812 A | 10/1998 | Nantz et al. |
| 5,827,703 A | 10/1998 | Debs et al. |
| 5,830,430 A | 11/1998 | Unger et al. |
| 5,830,878 A | 11/1998 | Gorman et al. |
| 5,834,439 A | 11/1998 | Haces et al. |
| 5,837,092 A | 11/1998 | Grieves et al. |
| 5,837,283 A | 11/1998 | McDonald et al. |
| 5,837,533 A | 11/1998 | Boutin |
| 5,840,710 A | 11/1998 | Lee et al. |
| 5,854,224 A | 12/1998 | Lockett et al. |
| 5,861,397 A | 1/1999 | Wheeler |
| 5,866,613 A | 2/1999 | Bergeron |
| 5,869,606 A | 2/1999 | Whittaker |
| 5,869,715 A | 2/1999 | Nantz et al. |
| 5,871,929 A | 2/1999 | Barnes |
| 5,877,309 A | 3/1999 | McKay et al. |
| 5,885,970 A | 3/1999 | Bennett et al. |
| 5,886,165 A | 3/1999 | Kandimalla et al. |
| 5,892,071 A | 4/1999 | Nantz et al. |
| 5,906,922 A | 5/1999 | Whittaker et al. |
| 5,908,635 A | 6/1999 | Thierry |
| 5,908,777 A | 6/1999 | Lee et al. |
| 5,916,807 A | 6/1999 | Bennett et al. |
| 5,919,772 A | 7/1999 | Szyf et al. |
| 5,925,623 A | 7/1999 | Nantz et al. |
| 5,929,226 A | 7/1999 | Padmapriya et al. |
| 5,935,936 A | 8/1999 | Fasbender et al. |
| 5,948,614 A | 9/1999 | Chatterjee |
| 5,948,767 A | 9/1999 | Scheule et al. |
| 5,948,925 A | 9/1999 | Keynes et al. |
| 5,962,533 A | 10/1999 | Bergeron, Jr. |
| 5,976,567 A | 11/1999 | Wheeler et al. |
| 5,977,084 A | 11/1999 | Szoka et al. |
| 5,977,306 A | 11/1999 | Grieve et al. |
| 5,985,558 A | 11/1999 | Dean et al. |
| 6,013,448 A | 1/2000 | Braxton et al. |
| 6,017,735 A | 1/2000 | O'Hare et al. |
| 6,020,202 A | 2/2000 | Jessee |
| 6,022,874 A | 2/2000 | Wheeler |
| 6,022,950 A | 2/2000 | Murphy |
| 6,030,626 A | 2/2000 | Kolattukudy et al. |
| 6,031,086 A | 2/2000 | Switzer |
| 6,056,938 A | 2/2000 | Unger et al. |
| 6,034,137 A | 3/2000 | Belloni et al. |
| 6,043,339 A | 3/2000 | Lin et al. |
| 6,051,429 A | 4/2000 | Hawley-Nelson et al. |
| 6,054,439 A | 4/2000 | Szyf et al. |
| 6,074,826 A | 6/2000 | Hogan et al. |
| 6,075,012 A | 6/2000 | Gebeyehu et al. |
| 6,086,913 A | 7/2000 | Tam et al. |
| 6,090,627 A | 7/2000 | Kemp et al. |
| 6,093,564 A | 7/2000 | Budowsky |
| 6,103,492 A | 8/2000 | Yu |

(56) References Cited

U.S. PATENT DOCUMENTS

| | | | |
|---|---|---|---|
| 6,110,662 A | 8/2000 | Foung et al. |
| 6,110,916 A | 8/2000 | Haces et al. |
| 6,126,965 A | 10/2000 | Kasid et al. |
| 6,180,784 B1 | 1/2001 | Wolff et al. |
| 6,211,140 B1 | 4/2001 | Sivik et al. |
| 6,214,804 B1 | 4/2001 | Felgner et al. |
| 6,251,390 B1 | 6/2001 | Harman et al. |
| 6,287,817 B1 | 9/2001 | Davis et al. |
| 6,333,433 B1 | 12/2001 | Banerjee et al. |
| 6,335,199 B1 | 1/2002 | Bischoff et al. |
| 6,346,516 B1 | 2/2002 | Banerjee et al. |
| 6,350,796 B1 | 2/2002 | Dworak et al. |
| 6,376,248 B1 | 4/2002 | Hawley-Nelson et al. |
| 6,387,395 B1 | 5/2002 | Eppstein et al. |
| 6,399,663 B1 | 6/2002 | Haces et al. |
| 6,495,518 B1 | 12/2002 | Hawiger et al. |
| 6,503,945 B2 | 1/2003 | Banerjee et al. |
| 6,521,455 B2 | 2/2003 | O'Hare et al. |
| 6,541,649 B2 | 4/2003 | Banerjee et al. |
| 6,716,882 B2 | 4/2004 | Haces et al. |
| 6,733,777 B2 | 5/2004 | Erbacher et al. |
| 6,773,920 B1 | 8/2004 | Dalby et al. |
| 6,890,554 B2 | 5/2005 | Jessee et al. |
| 6,989,434 B1 | 1/2006 | Gebeyehu et al. |
| 7,074,556 B2 | 7/2006 | Li et al. |
| 7,145,039 B2 | 12/2006 | Chu et al. |
| 7,166,298 B2 | 1/2007 | Jessee et al. |
| 7,166,745 B1 | 1/2007 | Chu et al. |
| 7,173,154 B2 | 2/2007 | Chu et al. |
| 7,323,594 B2 | 1/2008 | Chu et al. |
| 7,470,817 B2 | 12/2008 | Chu et al. |
| 7,479,573 B2 | 1/2009 | Chu et al. |
| 7,531,676 B2 | 5/2009 | Eaton et al. |
| 7,601,872 B2 | 10/2009 | Chu et al. |
| 7,915,450 B2 | 3/2011 | Chu et al. |
| 8,158,827 B2 | 4/2012 | Chu et al. |
| 8,785,200 B2 | 7/2014 | Chu et al. |
| 9,358,300 B2 | 6/2016 | Chu et al. |
| 2002/0028447 A1 | 3/2002 | Li et al. |
| 2002/0039765 A1 | 4/2002 | O'Hare et al. |
| 2002/0062044 A1 | 5/2002 | Banerjee et al. |
| 2002/0062489 A1 | 5/2002 | Silver et al. |
| 2002/0077305 A1 | 6/2002 | Jessee et al. |
| 2002/0086849 A1 | 7/2002 | Gebeyehu et al. |
| 2002/0106378 A1 | 8/2002 | O'Hare et al. |
| 2002/0156049 A1 | 10/2002 | Haces et al. |
| 2003/0069173 A1 | 4/2003 | Hawley-Nelson et al. |
| 2003/0144230 A1 | 7/2003 | Hawley-Nelson et al. |
| 2004/0152770 A1 | 8/2004 | Haces et al. |
| 2004/0176282 A1 | 9/2004 | Dalby et al. |
| 2005/0014962 A1 | 1/2005 | Gebeyehu et al. |
| 2005/0164391 A1 | 7/2005 | Chu et al. |
| 2005/0164971 A1 | 7/2005 | Chu et al. |
| 2005/0164972 A1 | 7/2005 | Chu et al. |
| 2005/0208657 A1 | 9/2005 | Dalby et al. |
| 2005/0260757 A1 | 11/2005 | Gebeyehu et al. |
| 2006/0228406 A1 | 10/2006 | Chiou et al. |
| 2006/0257858 A1 | 11/2006 | Chiou et al. |
| 2007/0202598 A1 | 8/2007 | Chu et al. |
| 2007/0202600 A1 | 8/2007 | Chu et al. |
| 2009/0143583 A1 | 6/2009 | Chu et al. |
| 2009/0163436 A1 | 6/2009 | Satishchandran |
| 2010/0159593 A1 | 6/2010 | Chu et al. |
| 2011/0244026 A1 | 10/2011 | Guild et al. |
| 2013/0203151 A1* | 8/2013 | Balsitis |

FOREIGN PATENT DOCUMENTS

| | | |
|---|---|---|
| DE | 0290877 | 6/1991 |
| DE | 4411588 | 9/1995 |
| DE | 4411594 | 12/1995 |
| EP | 2046720 | 7/1936 |
| EP | 0000406 | 1/1979 |
| EP | 0168930 | 1/1986 |
| EP | 0187702 | 7/1986 |
| EP | 0329822 B1 | 8/1989 |
| EP | 0359347 | 3/1990 |
| EP | 0394111 | 10/1990 |
| EP | 0304111 | 10/1991 |
| EP | 0544292 | 6/1993 |
| EP | 0821059 | 1/1998 |
| EP | 0846680 | 6/1998 |
| EP | 0684315 B1 | 6/2002 |
| EP | 1275735 | 1/2003 |
| EP | 1187807 | 7/2007 |
| EP | 1829856 | 9/2007 |
| FR | 1146332 | 7/1915 |
| FR | 1567214 | 5/1969 |
| GB | 0823303 | 11/1959 |
| GB | 892413 | 3/1962 |
| GB | 901187 | 7/1962 |
| JP | 08509953 | 10/1996 |
| JP | 09509402 | 9/1997 |
| JP | 09510435 | 10/1997 |
| JP | 10152461 | 6/1998 |
| JP | 10506901 | 7/1998 |
| JP | 10510813 | 10/1998 |
| JP | 2001525419 | 12/2001 |
| WO | WO-1987/02061 | 4/1987 |
| WO | WO-1994/02499 | 2/1989 |
| WO | WO-1990/009180 | 8/1990 |
| WO | WO-1990/009786 | 9/1990 |
| WO | WO-1990/101092 | 10/1990 |
| WO | WO-1991/004668 | 4/1991 |
| WO | WO-1991/004753 | 4/1991 |
| WO | WO-1991/007947 | 6/1991 |
| WO | WO-1991/008191 | 6/1991 |
| WO | WO-1991/015501 | 10/1991 |
| WO | WO-1991/016024 | 10/1991 |
| WO | WO-1991/017424 | 11/1991 |
| WO | WO-1992/006188 | 4/1992 |
| WO | WO-1992/006200 | 4/1992 |
| WO | WO-1992/013570 | 8/1992 |
| WO | WO-1992/020697 | 11/1992 |
| WO | WO-1992/021752 | 12/1992 |
| WO | WO-1992/022635 | 12/1992 |
| WO | WO-1993/003709 | 3/1993 |
| WO | WO-1993/005162 | 3/1993 |
| WO | WO-1993/007282 | 4/1993 |
| WO | WO-1993/007283 | 4/1993 |
| WO | WO-1993/008130 | 4/1993 |
| WO | WO-1993/014778 | 8/1993 |
| WO | WO-1993/019768 | 10/1993 |
| WO | WO-1994/002499 A1 | 2/1994 |
| WO | WO-1994/004696 | 3/1994 |
| WO | WO-1994/005624 | 3/1994 |
| WO | WO-1994/007899 | 4/1994 |
| WO | WO-1994/008004 | 4/1994 |
| WO | WO-1994/014475 | 7/1994 |
| WO | WO-1994/017093 | 8/1994 |
| WO | WO-1994/023751 | 10/1994 |
| WO | WO-1994/027433 A1 | 12/1994 |
| WO | WO-1994/027435 | 12/1994 |
| WO | WO-1994-002397 | 1/1995 |
| WO | WO-1995/02698 | 1/1995 |
| WO | WO-1995/016028 A1 | 6/1995 |
| WO | WO-1995/016664 | 6/1995 |
| WO | WO-1995/017373 | 6/1995 |
| WO | WO-1995/020682 | 8/1995 |
| WO | WO-1995/021259 | 8/1995 |
| WO | WO-1995/024221 | 9/1995 |
| WO | WO-1995/031557 | 11/1995 |
| WO | WO-1996/001841 | 1/1996 |
| WO | WO-1996/005218 | 2/1996 |
| WO | WO-1996/008723 | 3/1996 |
| WO | WO-1996/010038 | 4/1996 |
| WO | WO-1996/010640 | 4/1996 |
| WO | WO-1996/015811 | 5/1996 |
| WO | WO-1996/018372 | 6/1996 |
| WO | WO-1996/022321 | 7/1996 |
| WO | WO-1996/022765 | 8/1996 |
| WO | WO-1996/026179 | 8/1996 |
| WO | WO-1996/029337 | 9/1996 |
| WO | WO-1996/031549 | 10/1996 |

(56) References Cited

FOREIGN PATENT DOCUMENTS

| WO | WO-1996/032474 | 10/1996 |
|---|---|---|
| WO | WO-1996/035706 | 11/1996 |
| WO | WO-1996/040961 | 12/1996 |
| WO | WO-1997/002061 A1 | 1/1997 |
| WO | WO-1997/005265 | 2/1997 |
| WO | WO-1997/009451 | 3/1997 |
| WO | WO-1997/042819 | 11/1997 |
| WO | WO-1998/002190 | 1/1998 |
| WO | WO-1998/006736 | 2/1998 |
| WO | WO-1998/014439 | 4/1998 |
| WO | WO-1998/019709 | 5/1998 |
| WO | WO-1998/029541 | 7/1998 |
| WO | WO-1998/032866 | 7/1998 |
| WO | WO-1998/040499 | 9/1998 |
| WO | WO-1998/040502 | 9/1998 |
| WO | WO-1998/047912 | 10/1998 |
| WO | WO-1999/002190 | 1/1999 |
| WO | WO-1999/005302 | 2/1999 |
| WO | WO-1999/011809 | 3/1999 |
| WO | WO-1999/024559 | 5/1999 |
| WO | WO-1999/029712 | 6/1999 |
| WO | WO-1999/041410 | 8/1999 |
| WO | WO-1999/046400 | 9/1999 |
| WO | WO-2000/012454 | 3/2000 |
| WO | WO-2000/027795 | 5/2000 |
| WO | WO-2000/058488 | 10/2000 |
| WO | WO-2000/064858 | 11/2000 |
| WO | WO-2001/007548 | 2/2001 |
| WO | WO-2002/034879 | 5/2002 |
| WO | WO-2004/0063342 | 7/2004 |
| WO | WO-2004/0105697 | 12/2004 |

OTHER PUBLICATIONS

Aumailley, Monique et al., "Cell attachment properties of collagen type VI and Arg-Gly-Asp dependent binding to its alpha 2(VI) and alpha 3(VI) chains", *Experimental Cell Research*, vol. 181, No. 2, Apr. 1989, 463-474.

Banerjee, Rajkumar et al., "Design,Synthesis, and Transfection Biology of Novel Cationic Glycolipids for Use in Liposomal Gene Delivery", *Journal of Medicinal Chemistry*, vol. 44, No. 24, 2001, 4176-4185.

Banerjee, Rajkumar et al., "Novel Series of Non-Glycerol-Based Cationic Transfection Lipids for Use in Liposomal Gene Delivery", *Journal of Medicinal Chemistry*, vol. 42, No. 21, Oct. 1, 1999, 4292-4299.

Behr, Jean-Paul et al., "Efficient Gene Transfer Into Mammalian Primary Endocrine Cells with Lipopolyamine-Coated DNA", *Proceedings of the National Academy of Sciences (PNAS)*, vol. 86, Sep. 1989, 6982-6986.

Behr, Jean-Paul , "Gene Transfer with Synthetic Cationic Amphiphiles:Prospects for Gene Therapy", *Bioconjugate Chemistry*, vol. 5, No. 5, American Chemical Society, Sep. 1994, 382-389.

Behr, Jean-Paul , "Synthetic Gene-Transfer Vectors" *Accounts of Chemical Research*, vol. 26, No. 5, 1993, 274-278.

Bennett, C. F. et al., "Cationic lipids enhance cellular uptake and activity of phosphorothioate antisense oligonucleotides", *Molecular Pharmacology*, vol. 41, 1992, 1023-1033.

Bennett, Michael J. et al., "Cationic Lipid-Mediated Gene Delivery to Murine Lung: Correlation of Lipid Hydration with in Vivo Transfection Activity" *Journal of Medicinal Chemistry*, vol. 40, No. 25, 1997, 4069-4078.

Blagbrough, I.S. et al., "Polyamines and novel polyamine conjugates interact with DNA in ways that can be exploited in non-viral gene therapy", *Biochemical Society Transactions*, Polyamines and Their Role in Human Disease, vol. 31, Part 2, 2003, pp. 397-406.

Bonfanti, Marina et al., "p21WAF1-derived Peptides Linked to an Internalization Peptide Inhibit Human Cancer Cell Growth", *Cancer Research*, vol. 57, No. 8, Apr. 15, 1997, 1442-1446.

Brunette, Elisa et al., "Lipofection does not require the removal of serum" *Nucleic Acids Research*, vol. 20, No. 5, Mar. 11, 1992, 1151.

Budker, V. et al., "Protein/Amphipathic Polyamine Complexes Enable Highly Efficient Transfection with Minimal Toxicity", *Biotechniques*, vol. 23, No. 1, Jul. 1997, 139-147.

Butler, George B. et al., "Preparation and Polymerization of Unsaturated Quaternary Ammonium Compounds", *J. Am. Chem. Soc.*, vol. 71, No. 9, 1949, 3120-3122.

Caminati, Gabriella et al., "Photophysical Investigation of Starburst Dendrimers and Their Interactions with Anionic and Cationic Surfactants" *Journal of the American Chemical Society*, vol. 112, No. 23, Nov. 1990, 8515-8522.

Ciccarone, V. et al., "Cationic Liposome-Mediated Transfection of Eukaryotic Cells: High Efficiency Nucleic Acid Delivery with Lipofectin, Lipofectace, and Lipofectamine Reagents.", *The FASEB Journal*, vol. 7, No. 7, Abstract No. 454, Abstracts, Federation of American Societies for Experimental Biology, 1993, A1131.

Ciccarone, Valentina et al., "DMRIE-C reagent for transfection of suspension cells and for RNA transfections", Focus, vol. 17, No. 3, Sep. 1995, 84-87.

Deamer, D. W. et al., "Liposome Preparation: Methods and Mechanisms", in Liposomes, Marc J. Ostro, ed., Marcel Dekker, Inc. NY, 1983, 27-51.

Demeneix, B. A. et al., "Gene transfer into intact vertebrate embryos", International Journal of Developmental Biology, vol. 35, 1991, 481-484.

Duzgunes, Nejat et al., "Fusion of Liposomes Containing a Novel Cationic Lipid, N-[2,3-(Dioleyloxy)propyl]-N,N,N-trimethylammonium: Induction by Multivalent Anions and Asymmetric Fusion with Acidic Phospholipid Vesicles", Biochemistry, vol. 28, No. 23, American Chemical Society, 1989, 9179-9184.

Duzgunes, Nejat et al., "Intracellular Delivery of Nucleic Acids and Transcription Factors by Cationic Liposomes", Meth. Enzymol., vol. 221, 1993, 303-317.

Dwarki, V. J. et al., "Cationic Liposome-Mediated RNA Transfection", Methods in Enzymology, vol. 217, 1993, 644-654.

Eytan, Gera D. , "Use of Liposomes for reconstitution of biological functions", Biochimica et Biophysica Acta(BBA)—Reviews on Biomembranes, vol. 694, No. 2, Oct. 20, 1982, 185-202.

Felgner, P. L. , "Cationic Lipid/Polynucleotide Condensates for in vitro and in Vivo Polynucleotide Delivery—The Cytofectins", J. Liposome Research, vol. 3, No. 1, 1993, 3-16.

Felgner, P. L. et al., "Cationic liposome-mediated transfection", Focus, vol. 11, Life Technologies, Inc., 1989, 21-25.

Felgner, P. L. et al., "Gene Therapeutics", Nature, vol. 349, Macmillan Journals, Ltd., Jan. 24, 1991, 351-352.

Felgner, Philip L. et al., "Cationic liposome-mediated transfection", Nature, vol. 337, No. 6205, Jan. 26, 1989, 387-388.

Felgner, Philip L. et al., "Lipofection: A Highly Efficient, Lipid-Mediated DNA Transfection Procedure", Proceedings of the National Academy of Sciences (PNAS), vol. 84, 1987, 7413-7417.

Gao, et al., "Potentiation of Cationic Liposome-Mediated Gene Delivery by Polycations", Biochemistry, vol. 35, 1996, 1027-1036.

Ghonaim, H.M. , "Very Long Chain N4,N9-Diacyl Spermines: Non-Viral Lipopolyamine Vectors for Efficient Plasmid DNA and siRNA Delivery", Pharmaceutical Research, vol. 26, No. 1, Jan. 2009, pp. 19-31.

Goldfarb, David et al., "Pathways for the nuclear transport of proteins and RNAs", Trends in Cell Biology, vol. 1, No. 1, Jul. 1991, 20-24.

Goldman, Corey K. et al., "In vitro and in vivo gene delivery mediated by a synthetic polycationic amino polymer", Nature Biotechnology, vol. 15, Nature America Publishing, May 1, 1997, 462-466.

Gorman, C. , "High Efficiency Gene Transfer into Mammalian Cells", DNA Cloning, vol. II, Jul. 1985, 143-190.

Harrison, G. S. et al., "Optimization of Gene Transfer Using Cationic Lipids in Cell Lines and Primary Human CD4 and CD34 Hematopoietic Cells", BioTechniques, vol. 19, Eaton Publishing Company, 1995, 816-823.

Hawley-Nelson, Pamela et al., "Lipofectamine Reagent: A New, Higher Efficiency Polycationic Liposome Transfection Reagent", Focus, vol. 15, No. 3, Life Technologies Inc., 1993, 73-79.

(56) References Cited

OTHER PUBLICATIONS

Hogrefe, H. et al., "Novel PCR Enhancing Factor Improves Performance of Pfu DNA Polymerase", Stratagene Strategies 10:, Stratagene Cloning Systems, Aug. 1997, 93-96.

Holt, C. E. et al., "Lipofection of cDNAs in the Embryonic Vertebrate Central Nervous System", Neuron, vol. 4, Cell Press, 1990, 203-214.

Hope, M. J. et al., "Generation of Multilamellar and Unilamellar Phospholipid Vesicles", Chem. Phys. Lipids 40:, Elsevier Scientific Publishers Ireland, Ltd., 1986, 89-107.

Huang, L. et al., "Liposome and Immunoliposome Mediated Delivery of Proteins and Peptides", Targeting of Drugs 3—The Challenge of Peptides and Proteins, Gregoriadis, G. and Florence, AT. (eds.), Plenum Press, New York, NY., 1992, 45-50.

Ito, A. et al., "Synthetic cationic amphiphiles for liposome-mediated DNA transfection", Biochemistry International, vol. 22, Oct. 1990, 235-241.

Kim, S. et al., "Preparation of Multivesicular Liposomes", Biochim. Biophys. Acta, vol. 728, 1983, 339-348.

Legendre, Jean-Yves et al., "Delivery of Plasmid DNA into Mammalian Cell Lines Using pH-Sensitive Liposomes: Comparison with Cationic Liposomes", Pharmaceutical Research, vol. 9, No. 10, Oct. 1992, 1235-1242.

Litzinger, David C. et al., "Amphipathic poly(ethylene glycol) 5000-stabilized dioleoylphosphatidylethanolamine liposomes accumulate in spleen", Biochimica et Biophysica Acta, vol. 1127, 1992, 249-254.

Mack, Karl D., "Cationic lipid enhances in vitro Receptor-mediated Transfection", The American Journal of the Medical Sciences, vol. 307, No. 2, Feb. 1994, 138-143.

Malone, Robert W. et al., "Cationic Llposome-Mediated RNA Transfection", Proceedings of the National Academy of Sciences (PNAS), vol. 86, No. 16, Aug. 15, 1989, 6077-6081.

Mazur, W. et al., "The Efficiency of Lipofectin-Mediated Gene Transfer into Porcine and Human Coronary Smooth Muscle Cells is Dramatically Improved by the Influenza Virus Hemagglutinin Antigen", Journal of the American College of Cardiology, Sppl. 21, Abstract No. 889-31, 1993, 186A.

McCluskie, M. J. et al., "Direct gene transfer to the respiratory tract of mice with pure plasmid and lipid-formulated DNA", Antisense Nucleic Acid Drug Dev., vol. 8, No. 5., Oct. 1998, 401-414.

PCT/US2015/040651, , "International Search Report and Written Opinion", dated Oct. 19, 2015, 14 Pages.

Poste, George et al., "Lipid vesicles as carriers for introducing biologically active materials into cells", Methods in Cell Biology, vol. 14, 1976, 33-71.

Stewart, Mark J. et al., "Gene Transfer in Vivo with DNA-Liposome Complexes: Safety and Acute Toxicity in Mice", Human Gene Therapy, vol. 3, No. 3, 1992, 267-275.

Rose, John K. et al., "A new cationic liposome reagent mediating nearly quantitative transfection of animal cells", *Biotechniques*, vol. 10, No. 4, Apr. 1991, 520-525.

\* cited by examiner

US 10,792,362 B2

COMPOSITIONS AND METHODS FOR EFFICIENT DELIVERY OF MOLECULES TO CELLS

CROSS REFERENCE TO RELATED APPLICATIONS

This application is a continuation of U.S. Nonprovisional application Ser. No. 14/800,565 filed Jul. 15, 2015, which issued as U.S. Pat. No. 10,195,280 on Feb. 5, 2019, which application claims the right of priority under 35 U.S.C. § 119(e) to U.S. Provisional Application Ser. No. 62/024,918, filed Jul. 15, 2014, which is commonly owned with the present application and which the entire contents thereof are hereby expressly incorporated by reference as though fully set forth herein.

FIELD OF THE INVENTION

The present invention relates to lipid aggregates having at least two cationic lipids and having utility for forming complexes with biologically active nucleic acid molecules, particularly RNA molecules, for the improved delivery thereof into a wide variety of cells and tissues.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Lipid aggregates such as liposomes have been found to be useful as delivery agents to introduce macromolecules, such as DNA, RNA, proteins, and small chemical compounds such as small molecules or pharmaceutically active molecules, to cells and tissues in laboratory and clinical research settings. In particular, lipid aggregates comprising cationic lipid components have been shown to be especially effective for delivering anionic molecules to cells. In part, the effectiveness of cationic lipids, and positively charged complexes formed with cationic lipids, is thought to result from enhanced affinity for cells, many of which bear a net negative charge. Also in part, the net positive charge on lipid aggregates comprising a cationic lipid enables the aggregate to bind polyanions, such as nucleic acids. Lipid aggregates containing DNA and RNA are known to be effective agents for efficient transfection of target cells Messenger RNA (mRNA)-based gene delivery has generated much interest in recent years. mRNA transfection has several advantages plasmid or vector-based transfection methodologies, including a lack of requirement for nuclear entry, which poses a significant barrier to plasmid DNA (pDNA) delivery, especially in non-dividing cells. mRNA also has a negligible chance of integrating into the host genome. (mRNA) is frequently applied as a gene delivery molecule in the field of cancer immunotherapy and stem cell-based research as an alternative to pDNA. In addition, a rapidly growing interest in using mRNA instead of pDNA for iPS cell reprogramming, genome editing (CRISPR, TALEN) and vaccine development has emerged.

Despite the advantages of mRNA transfection over DNA, there are few commercially available reagents that can efficiently and consistently yield high transfection efficiencies of cargo mRNA over a wide variety of cell types and lineages, such as primary cells, neuronal cells, blood cells, stem cells and difficult to transfect cell lines.

Thus, there exists a need for lipid aggregate formulations that are capable of delivery a variety of cargos to a wide spectrum of cell lineages and difficult to transfect cells.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DESCRIPTION OF THE INVENTION

Figure 1:
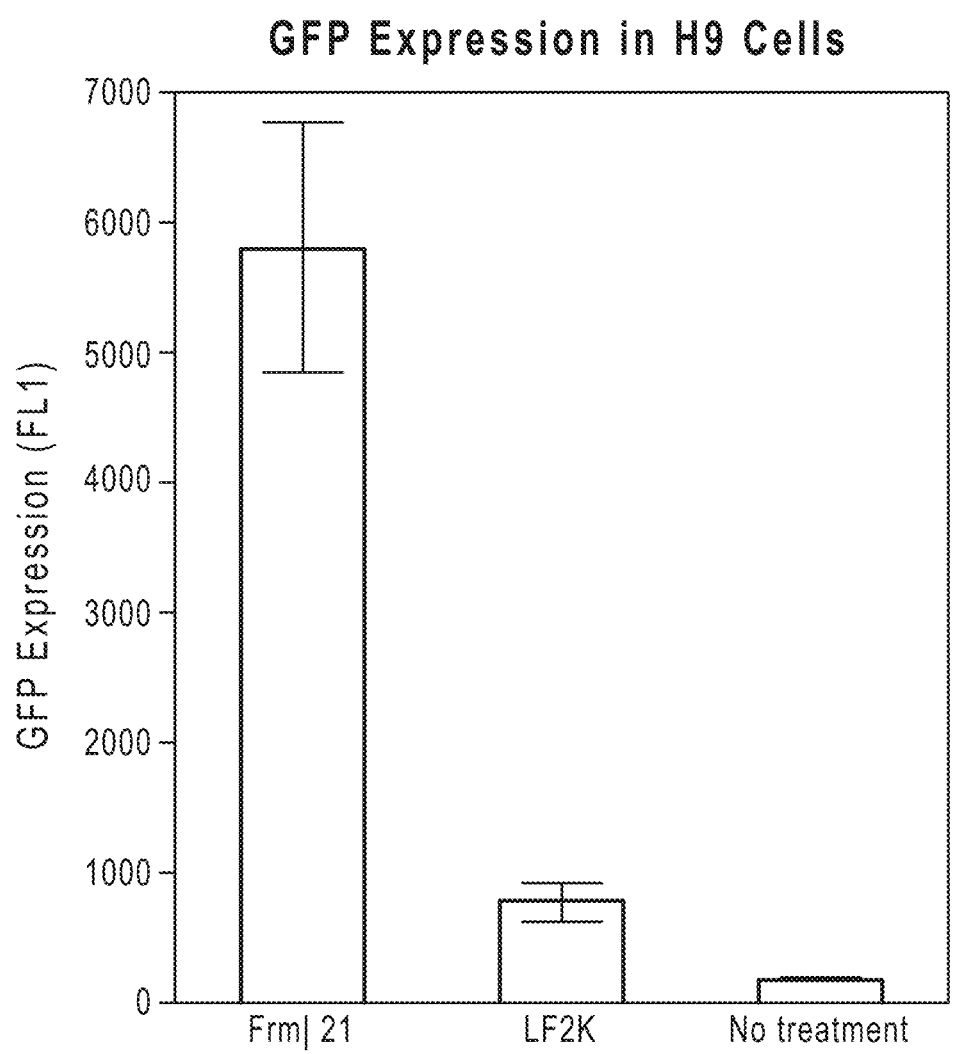
FIG. 1 shows the improved transfection efficiency of a lipid aggregate in accordance with one embodiment when compared to a commercially available cationic lipid-based transfection reagent, Lipofectamine® 2000 (LF2K)

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

The present invention provides novel formulations of lipid aggregates and methods for the use thereof to deliver target molecules to a cell or to a tissue. The invention includes a first cationic lipid and at least a second cationic lipid with one or more additional cationic lipid that, when formulated with at least one neutral lipid, optionally with a second neutral lipid, are part of a cationic lipid aggregate, such as a liposome. In particular, the lipid aggregates that form the basis of the present invention are suitable for use in the formation of cationic complexes with one or more specific target molecules, which complexes can then be used for the delivery of the target molecule to a cultured cell or to a tissue in vitro or, in some embodiments, in vivo.

Definitions:

In the description that follows, a number of terms used in cell culture and recombinant DNA technology are utilized extensively. In order to provide a clear and more consistent understanding of the specification and claims, including the scope to be given such terms, the following definitions are provided.

The term "introduction" of a macromolecule or compound into culture refers to the provision of the macromolecule or compound into the culture medium. This may also be referred to as "contacting" a macromolecule with a culture, a cell or a tissue, such as will be readily apparent to one skilled in the art.

The term "introduction" of a macromolecule, a cargo, a biologically relevant molecule, a compound, or the like, into at least one cell refers to the provision of a macromolecule, a cargo, a biologically relevant molecule, a compound, or the like to a cell, such that the macromolecule, cargo or compound becomes internalized in the cell. For example, a macromolecule or compound can be introduced into a cell using transfection, transformation, injection, and/or liposomal introduction, and may also be introduced into a cell using other methods known to those of ordinary skill in the art. Preferably, in the context of the embodiments described herein, a macromolecule or compound is introduced into a cell by liposomal introduction. The macromolecule is preferably a protein, polypeptide, or nucleic acid. In some preferred embodiments, the macromolecule may also be a nucleic acid, such as a DNA molecule or an RNA molecule.

The term "cargo", when used herein in the context of the delivery of a cargo into the interior of a cell, such as by mean of transfection, generally refers to any substance that is to be conveyed to the interior of a cell, either in culture in a laboratory or in a tissue in an animal or a human, such as the use thereof in a therapeutic modality. A cargo may, depending on the application, be a macromolecule such as a nucleic acid (DNA or RNA), a protein, or a peptide, or may be a drug or other organic small molecule.

The term "macromolecule," as used herein, encompasses a biomolecule. In one embodiment, the term macromolecule refers to nucleic acid. In a preferred embodiment, the term macromolecule refers to deoxyribonucleic acid (DNA) and ribonucleic acid (RNA). In some embodiments, the term macromolecule refers to DNA. In certain preferred though non-limiting embodiments the term macromolecule refers to an RNA molecule, generally one that has been synthesized using recombinant DNA techniques. In some embodiments, RNA molecules used in accordance with the invention described below may include at least one, optionally more than one, at least two, optionally more than two, at least three, optionally more than three, at least four, optionally more than four, or at least five expressible nucleic acid sequence(s), including at least one open reading frame operably linked to one or more nucleic acid sequence required for the translation thereof from the expressible nucleic acid sequence. An RNA molecule may be any type of RNA molecule, including but not limited to an mRNA, an siRNA, an miRNA, an antisense RNA, a guide RNA (gRNA) used in conjunction with a genome editing system, a ribozyme, or any other type or species of RNA molecule familiar to those skilled in the art without limitation, that would be sought to be delivered to the interior of a cell.

The term "transfection" is used herein to mean the delivery of nucleic acid, protein or other cargo or macromolecule to a target cell in culture or to a tissue, such that the nucleic acid, protein, cargo or other macromolecule is delivered to the interior of the cell or constituent cells of a tissue with the purpose of modifying at least one biological function thereof.

The term "expressible nucleic acid" as used herein includes both DNA and RNA without regard to molecular weight, and the term "expression" means any manifestation of the functional presence of the nucleic acid within the cell including, without limitation, both transient expression and stable expression.

The term "cell" as used herein refers includes all types of eukaryotic and prokaryotic cells. In preferred embodiments, the term refers to eukaryotic cells, especially cells grown in culture, or cells found in a tissue in an animal or a human. In preferred embodiments, a cell refers to a mammalian cell. In certain exemplary though non-limiting embodiments, the term "cell" is meant to refer to any cell and cell line that is routinely used in research and clinical settings, and may include immortalized cell lines, transformed cell lines, or primary cells, without limitation.

The phrase "difficult to transfect", or variants thereof, when used in the context of transfection procedures and reagents, generally refers to any cell or cell line that typically exhibits less than 60% transfection efficiency when transfected using standard commercially available transfection reagents such as, e.g., cationic lipids. Cells defined as difficult to transfect include primary cells, such as stem cells (including both embryonic stem cells and induced-pluripotent stem cells), progenitor cells, neuronal cells and other cell types derived from neural tissues, primary blood cells ("PBMC"), HUVEC, and the like, as well as certain cell lines that, while established, are recognized in the art as being difficult to efficiently transfect using commercially available transfection reagent. Examples of difficult to transfect cell lines include, but are not limited to, PC12, HepG2, 3T3, LNCaP, A549, Jurkat, and PC3, among others.

By "cell culture" or "culture" is meant the maintenance of cells in an artificial, in vitro environment.

"Kit" refers to transfection, RNA (including RNAi), cargo delivery or protein expression kits which include one or more of the reagents of the present invention or mixtures thereof optionally in combination with one or more reagents or components used achieve the desired performance of the kit (e.g., transfection of a cargo to a cell or a tissue). The kits may include one or more of the non-naturally occurring lipid aggregates described below, optionally with one or more additional cationic lipids or other transfections reagents. In some embodiments, the lipid aggregates may be provided in a single formulation. In other embodiments, the lipid aggregate components may be provided separately, with instruction to the user to combine the reagents at the time of use. Such kits may comprise a carrying means being compartmentalized to receive in close confinement one or more container means such as vials, test tubes and the like. Each of such container means comprises components or a mixture of components needed to perform transfection. Such kits may optionally include one or more components selected from any cargo molecules such as, e.g., nucleic acids (preferably one or more expression vectors, DNA molecules, RNA molecules or RNAi molecules), cells, one or more compounds of the present invention, lipid-aggregate forming compounds, transfection enhancers, biologically active substances, etc.

The term "combining" or "contacting" refers to the mixing or admixing of components, or to the addition of one component to another such that the constituent components are mixed or in close proximity or contact to one another.

The terms "polynucleotide" and "nucleic acid" are used interchangeably herein and may refer to any nucleic acid, including deoxyribonucleic acid (DNA) and ribonucleic acid (RNA). The terms will include the full range of polymers of single or double stranded nucleotides and includes nucleic acids (including DNA, RNA, and DNA-RNA hybrid molecules) that are isolated from a natural source; that are prepared in vitro, using techniques such as PCR amplification or chemical synthesis; that are prepared in vivo, e.g., via recombinant DNA technology; or that are prepared or obtained by any appropriate method. A nucleic acid typically refers to a polynucleotide molecule comprised of a linear strand of two or more nucleotides (deoxyribonucleotides and/or ribonucleotides) or variants, derivatives and/or analogs thereof. The exact size will depend on many factors, which in turn depends on the ultimate conditions of use, as is well known in the art. The nucleic acids of the present invention include without limitation primers, probes, oligonucleotides, vectors, constructs, plasmids, genes, transgenes, genomic DNA, cDNA, RNA, RNAi, siRNA, shRNA, stRna, PCR products, restriction fragments, and the like.

A polynucleotide/nucleic acid molecule may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein the terms "complexation," "complexation reaction," "complexation media" or the like, generally refer to a physiologically acceptable culture media or reaction in which a cargo, such as, e.g., a nucleic acid is complexed with a transfection reagent formulation, such as a lipid aggregate as described below, to form a supramolecular complex incorporating the cargo and the lipid aggregate. Typically, a cargo that is to be introduced into a cell for the purpose of expressing a protein is first complexed with a suitable transfection reagent (such as, e.g., a cationic lipid aggregate formulation) to form lipid/nucleic acid complexes or aggregates.

"Lipid aggregate" is a generic term that includes liposomes of all types, both unilamellar and multilamellar, as well as vesicles, micelles and more amorphous aggregates. A cationic lipid aggregate as used herein refers to a lipid aggregate comprising a combination of two or more cationic compounds having the structures and properties defined below, in combination with at least one, optionally more than one, non-cationic lipids (including neutral lipids), such that the lipid aggregate has a net positive charge under physiologic conditions in an aqueous solution. Cationic compounds of the present invention can form a lipid aggregate, in combination with one or more helper lipids such as one or more neutral lipids, which can then form a lipid-polyanion complex when mixed with a polyanion cargo molecule. The term "lipid-cargo" or "lipid-polyanion" generally refers to the noncovalent association between a lipid or lipid aggregate and a cargo or a polyanion, such as a nucleic acid (or other cargo molecule as defined elsewhere in the specification). A helper lipid is any lipid that is beneficially combined with a cationic lipid to form a lipid aggregate. Helper lipids can include cationic lipids other than those of this invention (a variety of which are known in the art), and neutral lipids. Neutral lipids are those that do not carry a net positive charge. They may be charge neutral species or zwitterionic. A lipid-polyanion complex is also referred to herein as a lipoplex.

A "liposomal composition" generally is a formulation that includes one or more liposomes. These formulations are typically colloids, but can be dried formulations as well. A liposome is a vesicular colloidal particle composed of self-assembled amphiphilic molecules. Liposomal compositions of the present invention typically include a cationic lipid and a helper lipid (i.e., a neutral lipid) that are processed using standard methods to form a liposome-containing colloid suspension.

Liposomal compositions of this invention are those containing two or more cationic compounds having the structures and properties defined below, in combination with at least one, optionally more than one neutral and/or helper lipids which are treated by standard methods known in the art to form liposomes. The compositions are treated, for example, by sonication, vigorous vortexing, extrusion, reverse evaporation, microfluidization and like methods. Liposomal compositions can be distinguished one from another by particle size measurements. Different compositions will exhibit differences in particle size and uniformity of particle size, e.g., average particle size, and polydispersity. Different compositions will exhibit differences in the extent of the composition that is in the form of liposomes. In some embodiments, liposomal compositions will exhibit particle size in the range 120 nm and 800 nm and will exhibit generally lower polydispersity. Lipoplex particle size (with cargo) may range from about 40 nm to 135 nm. In some embodiments, lipoplex particle size is 50 nm to 120 nm, 50 nm to 100 nm, 60 nm to 90 nm, 70 nm to 90 nm, or about 85 nm.

A "reporter gene" as used herein is a nucleic acid (either a DNA or an RNA) encoding a readily assayable protein. Assays can be qualitative, quantitative, manual, automated, semi-automated, etc. Non-limiting examples of reporter genes include: genes encoding R-galactosidase (lacZ), neomycin resistance, HIS3, luciferase (LUC), chloramphenicol acetyltransferase (CAT), R-glucuronidase (GUS), human growth hormone (hGH), alkaline phosphatase (AP), secreted alkaline phosphatase (SEAP), and fluorescent polypeptides such as GFP. Those skilled in the art will be able to select reporter genes appropriate for the host cell and application of interest. For reviews of vectors and reporter genes see Baneyx F. Recombinant protein expression in *Escherichia coli*. Curr Opin Biotechnol 10:411-421, 1999; Van Craenenbroeck K, Vanhoenacker P, Haegeman G. Episomal vectors for gene expression in mammalian cells. Eur. J. Biochem. 2000, September 267(18):5665-78; Soll D R, Srikantha T. Reporters for the analysis of gene regulation in fungi pathogenic to man. Curr Opin Microbiol. 1998, August 1(4):400-405; Possee R D. Baculoviruses as expression vectors. Curr Opin Biotechnol. 1997, October 8(5):569-72; and Mount R C, Jordan B E, Hadfield C. Reporter gene systems for assaying gene expression in yeast. Methods Mol Biol. 1996. 53:239-48.

Description of the Preferred Embodiments:

The lipid aggregates that form the basis of the present invention are particularly suited for the delivery of biologically active molecules the interior of a wide variety of cells, including but not limited to cell lines commonly used in research lab setting, as well as those cells lines and lineages that are typically considered "difficult to transfect". A variety of cells lineages that "difficult to transfect" are known in the art and what constitutes such a cell is readily recognized by a person having ordinary skill level in the art, but will, for the purposes of the present disclosure generally include any cell line, primary cell, or tissue that typically exhibits less than 60% transfection efficiency when transfected using currently available commercial transfection reagents, such as, by way of non-limiting example only, LIPOFECTAMINE®, LIPOFECTAMINE® 2000, LIPOFECTAMINE® 3000, RNAiMAX®, SUREFECT®, TRANSIT® Transfection Reagents, VIAFECT™ Transfection reagents, FUGENE® Transfection Reagents.

Non-limiting examples of difficult to transfect cells that may be suited to the use of the present lipid aggregates for the transfection of biologically active molecules to the interior thereof include primary cells, neurons, cells of neuronal lineage, lymphoid cells, T cells, B cells, cell lines derived from the aforementioned, and stem cells (both embryonic and induced pluripotent).

Accordingly, it is an object of the present to provide lipid aggregate composition suitable for use as transfection reagents that are capable of forming cationic complexes under physiologically relevant conditions with a variety of biologically active molecules, particularly though not limited to RNA molecules, include mRNA molecules, RNA molecules having one or optionally more than one expressible nucleic acid sequences encoding one or more proteins or polypeptides, or other DNA molecules, and which exhibit an improved transfection of at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 175%, 200%, 225%, 250%, 275%, 300%, 350%, 400%, 450%, 500%, 600%, 700%, 800%, or any interval therebetween, greater than that of presently available commercial lipid based reagent can presently achieve in such cells. It is yet a further object of the present invention to provide lipid aggregate compositions suitable for use as transfection reagents, which lipid aggregates are capable of forming cationic complexes under physiologically relevant conditions with a variety of biologically active molecules, particularly though not limited to RNA molecules, include mRNA molecules, RNA molecules having one or optionally more than one expressible nucleic acid sequences encoding one or more proteins or polypeptides, or other DNA molecules, and which exhibit an improved transfection of at least about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, 15, 10.5, 11, 12, 13, 14, 15 20-fold, or any interval therebetween, greater than that of presently available commercial lipid based reagent can presently achieve in such cells.

The cargo molecules delivered to the cell may be any biologically relevant macromolecule, including but not limited to negatively charged macromolecules which may include peptides, polypeptides, nucleic acids (including DNA, RNA, PNA and other synthetic nucleic acids) and various biologically active molecules or compositions. In the embodiments presented herein, the biologically active molecules retain biological activity after delivery.

In certain preferred though non-limiting embodiments, cargo molecules that may be particularly suited to for use as cargo carried by the lipid aggregate formulations described herein include nucleic acid molecules, including DNA or RNA molecules, in particular RNA molecules. In some embodiments, RNA molecules particularly suited for use as cargo carried by the lipid aggregate formulations described herein include RNA molecules having one or more expressible nucleic acid sequences, such one or more expressible nucleic acid sequences encoding a polypeptide. In other embodiments, RNA molecules suitable for cellular delivery with the instant lipid aggregate compositions may include RNAi molecules (such as, e.g., siRNA, miRNA, and the like), or guide RNA (gRNA) molecules used in certain genome editing systems as will be readily appreciated by the skilled artisan.

In some non-limiting embodiments, in particular those embodiments involving the use or introduction of one or more genome editing components, in particular gene editing components in the CRISPR pathway, RNA molecules particularly suited for use as cargo carried by the lipid aggregate formulations described herein can include "guide RNA" (gRNA) molecules, such as will be readily recognized by those skilled in the art.

In some embodiments, methods are provided that use the lipid aggregates of the present invention to deliver nucleic acid molecules into cells, including the delivery of RNA molecules generally or RNA molecules comprising at least one, optionally more than one, optionally up to about 5 expressible nucleic acid sequences that encode one or more proteins or polypeptides.

In one non-limiting aspect of the present invention, lipid aggregates suitable for use as a delivery agent of a cargo, such as a biologically active molecule such as a nucleic acid (DNA or RNA) or a protein to the interior of a cell in culture or in a tissue are provided. In some preferred though non limiting embodiments, the subject lipid aggregates are particularly suited for the delivery (transfection) of RNA to the interior of a cell in culture or in a tissue are provided.

The lipid aggregates that form the basis of the present disclosure include a first cationic lipid and at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein each of said first and second cationic lipids have the structure:

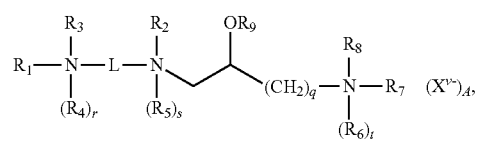

and salts thereof; where:

$R_1$ and $R_2$, independently, are an alkyl, alkenyl or alkynyl groups, having from 8 to 30 carbon atoms;

alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is —$(CH_2)_q$—$N(R_6)_rR_7R_8$;

$R_3$ and $R_4$, independently, are hydrogens, —$(CH_2)_p$—$NH_2$, an alkyl, an alkenyl or alkynyl groups optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

p and q are independently an integer ranging from 1 to 6, inclusive;

$X^v$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{$—$(CH_2)_k$—Y—$(CH_2)_m\}_p$—, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both $OR_{13}$ and $N(R_{13})_2$ groups.

The synthesis of these compounds and methods for the preparation of lipid aggregates incorporating same may be achieved by any means known to those skilled in the art without limitation. Exemplary though non-limiting methods to synthesize such compounds, and methods for the formation of lipid aggregates incorporating same, may be found in, for example, U.S. Pat. No. 7,166,745 and PCT Publication No. WO 00/27795, both of which are expressly incorporated by reference in their entirety as though fully set forth herein.

In some embodiments, the lipid aggregates that form the basis of the present invention may further optionally include one, optionally more than one additional cationic lipid selected from the list consisting of TMTPS, DOGS, DPPES, DOTMA, DOTAP, DDAB, DMRIE, DOSPA, and DOSPER.

In some embodiments of the present lipid aggregates, the first cationic lipid used in the formation thereof may be Dihydroxyl-dimyristylspermine tetrahydrochloride (hereinafter referred to as "DHDMS"))) having the structure:

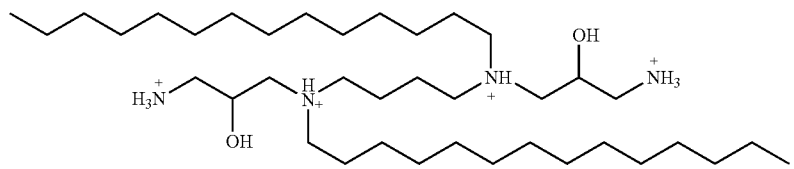

In some embodiments of the present lipid aggregates, the second cationic lipid used in the formation thereof may be hydroxyl-dimyristylspermine tetrahydrochloride (hereinafter referred to as "HDMS") having the structure:

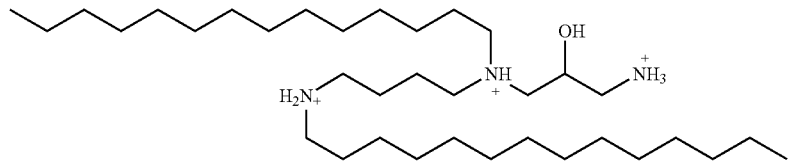

In some embodiments of the present lipid aggregates, the first cationic lipid used in the formation thereof may be DHDMS having the structure:

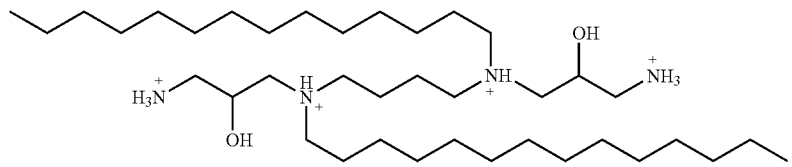

and the second cationic lipid used in the formation thereof may be HDMS having the structure:

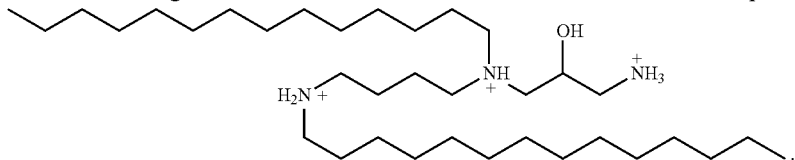

In some embodiments, the first and optional second neutral lipids may be selected from the following; DOPE, cholesterol or DOPC. In one embodiment, the first neutral lipid maybe one of cholesterol, DOPE or DOPC. In an embodiment, the first neutral lipid is cholesterol. In an embodiment, the first neutral lipid is DOPE. In an embodiment, the first neutral lipid is DOPC.

In one embodiment, the optional second neutral lipid maybe one of cholesterol, DOPE or DOPC, except that the second neutral lipid and the first neutral lipid described above are not the same. In an embodiment, the optional second neutral lipid is cholesterol. In an embodiment, the optional second neutral lipid is DOPE. In an embodiment, the optional second neutral lipid is DOPC.

In an embodiment, the first neutral lipid may be cholesterol and the optional second neutral lipid may be DOPE. In one embodiment, the first neutral lipid may be cholesterol and the optional second neutral lipid may be DOPC. In one embodiment, the first neutral lipid may be DOPE and the optional second neutral lipid may be DOPC.

In some embodiments, the molar ratio of the first cationic lipid in the lipid aggregate may be in the range of about 0.1 to about 0.4. In some embodiments, the molar ratio of the first cationic lipid in the lipid aggregate may be about 0.1, about 0.2, about 0.25, about 0.3 or about 0.4, or any range falling therebetween.

In some embodiments, the molar ratio of DHDMS in the lipid aggregate may be in the range of about 0.1 to about 0.4. In some embodiments, the molar ratio of the first cationic lipid in the lipid aggregate may be about 0.1, about 0.2, about 0.25, about 0.3 or about 0.4, or any range falling therebetween.

In some embodiments, the molar ratio of the second cationic lipid in the lipid aggregate may be in the range of about 0.1 to about 0.4. In some embodiments, the molar ratio of the second cationic lipid in the lipid aggregate may be about 0.1, about 0.2, about 0.25, about 0.3 or about 0.4, or any range falling therebetween.

In some embodiments, the molar ratio of HDMS in the lipid aggregate may be in the range of about 0.1 to about 0.4. In some embodiments, the molar ratio of the second cationic lipid in the lipid aggregate may be about 0.1, about 0.2, about 0.25, about 0.3 or about 0.4, or any range falling therebetween.

In some embodiments, the molar ratio of DHDMS is about 0.1 to about 0.4. In some embodiments, the molar ratio of DHDMS is about 0.1, about 0.2, about 0.25, about 0.3, about 0.4, or any range falling therebetween.

In some embodiments, the molar ratio of HDMS is about 0.1 to about 0.4. In some embodiments, the molar ratio of HDMS is about 0.1, about 0.2, about 0.25, about 0.3, about 0.4, or any range falling therebetween.

In some embodiments, the molar ratio of the first neutral lipid in the lipid aggregate may be in the range of about 0.1 to about 0.4. In some embodiments, the molar ratio of the first neutral lipid in the lipid aggregate may be about 0.1, about 0.2, about 0.25, about 0.3 or about 0.4, or any range falling therebetween.

In some embodiments, the molar ratio of the optional second neutral lipid in the lipid aggregate may be in the range of about 0.1 to about 0.4. In some embodiments, the molar ratio of the second neutral lipid in the lipid aggregate may be about 0.1, about 0.2, about 0.25, about 0.3 or about 0.4, or any range falling therebetween.

In some embodiments where no second neutral lipid is present in the lipid aggregates, the molar ratio of the first neutral lipid may be in the range of about 0.2 to about 0.8. In some embodiments where no second neutral lipid is present in the lipid aggregates, the molar ratio of the first neutral lipid may about 0.1, about 0.2, about 0.25, about 0.3, about 0.35, about 0.4, about 0.45, about 0.5, about 0.55, about 0.6, about 0.65, about 0.7, about 0.75, about 0.8, or any range falling therebetween.

In some embodiments, the molar ratio of cholesterol is about 0.1 to about 0.4. In some embodiments, the molar ratio of cholesterol is about 0.1, about 0.2, about 0.25, about 0.3, about 0.4, or any range falling therebetween.

In some embodiments, the molar ratio of DOPE is about 0.1 to about 0.4. In some embodiments, the molar ratio of DOPE is about 0.1, about 0.2, about 0.25, about 0.3, about 0.4, or any range falling therebetween.

In some embodiments, the molar ratio of DOPC is about 0.1 to about 0.4. In some embodiments, the molar ratio of DOPC is about 0.1, about 0.2, about 0.25, about 0.3, about 0.4, or any range falling therebetween.

In some embodiments, the molar ratio of cholesterol is about 0.2 to about 0.8. In some embodiments, the molar ratio of cholesterol is about 0.1, about 0.2, about 0.25, about 0.3, about 0.35, about 0.4, about 0.45, about 0.5, about 0.55, about 0.6, about 0.65, about 0.7, about 0.75, about 0.8, or any range falling therebetween.

In some embodiments, the molar ratio of DOPE is about 0.2 to about 0.8. In some embodiments, the molar ratio of DOPE is about 0.1, about 0.2, about 0.25, about 0.3, about 0.35, about 0.4, about 0.45, about 0.5, about 0.55, about 0.6, about 0.65, about 0.7, about 0.75, about 0.8, or any range falling therebetween.

In some embodiments, the molar ratio of DOPC is about 0.2 to about 0.8. In some embodiments, the molar ratio of DOPC is about 0.1, about 0.2, about 0.25, about 0.3, about 0.35, about 0.4, about 0.45, about 0.5, about 0.55, about 0.6, about 0.65, about 0.7, about 0.75, about 0.8, or any range falling therebetween.

In some embodiments, the molar ratio of DHDMS is about 0.1, 0.2, 0.25, 0.3, or 0.4 and molar ratio of cholesterol is about 0.1, 0.2, 0.25, 0.3, or 0.4. In some embodiments, the molar ratio of HDMS is about 0.1, 0.2, 0.25, 0.3, or 0.4 and molar ratio of DOPE is about 0.1, 0.2, 0.25, 0.3, or 0.4. In some embodiments, the molar ratio of DHDMS is about 0.1, the molar ratio of HDMS is about 0.4, the molar ratio of DOPE is about 0.1 and the molar ratio of cholesterol is about 0.4. In some embodiments, the molar ratio of DHDMS is about 0.25, the molar ratio of HDMS is about 0.25, the molar ratio of DOPE is about 0.4 and the molar ratio of cholesterol is about 0.1. In some embodiments, the molar ratio of DHDMS is about 0.3, the molar ratio of HDMS is about 0.1, the molar ratio of DOPE is about 0.3 and the molar ratio of cholesterol is about 0.3. In some embodiments, the molar ratio of DHDMS is about 0.4, the molar ratio of HDMS is about 0.1, the molar ratio of DOPE is about 0.4 and the molar ratio of cholesterol is about 0.1.

The composition of a variety of lipid formulations in accordance with several non-limiting embodiments of the invention are provided in Table I. The provision of these exemplary embodiments is in no way meant to limit the scope of the invention solely to those formulations disclosed. On the contrary, it is merely meant to provide a variety of possible lipid aggregate formulations that can be used in the practice of the present invention. Nevertheless, it will be apparent to one skilled in the art that the formulations may be changed or altered, and additional components (such as, e.g., additional cationic or neutral lipids, peptide targeting moieties, and the like) may be added, or one of the recited neutral lipids set forth in Table I may optionally be removed, and the resulting formulations will be within the spirit and scope of the invention as described herein.

TABLE I

Exemplary Lipid Aggregate Formulations According to Some Non-Limiting Embodiments (in Molar Percent)

| Formulation | DHDMS | HDMS | DOPE | Cholesterol |
|---|---|---|---|---|
| 1 | 0.1 | 0.1 | 0.4 | 0.4 |
| 2 | 0.1 | 0.25 | 0.25 | 0.4 |
| 3 | 0.1 | 0.25 | 0.4 | 0.25 |
| 4 | 0.1 | 0.4 | 0.1 | 0.4 |
| 5 | 0.1 | 0.4 | 0.25 | 0.25 |
| 6 | 0.1 | 0.4 | 0.4 | 0.1 |
| 7 | 0.1 | 0.3 | 0.3 | 0.3 |
| 8 | 0.2 | 0.4 | 0.2 | 0.2 |
| 9 | 0.2 | 0.2 | 0.2 | 0.4 |
| 10 | 0.2 | 0.2 | 0.4 | 0.2 |
| 11 | 0.25 | 0.4 | 0.1 | 0.25 |
| 12 | 0.25 | 0.4 | 0.25 | 0.1 |
| 13 | 0.25 | 0.1 | 0.25 | 0.4 |
| 14 | 0.25 | 0.1 | 0.4 | 0.25 |
| 15 | 0.25 | 0.25 | 0.1 | 0.4 |
| 16 | 0.25 | 0.25 | 0.4 | 0.1 |
| 17 | 0.3 | 0.1 | 0.3 | 0.3 |
| 18 | 0.3 | 0.3 | 0.1 | 0.3 |
| 19 | 0.3 | 0.3 | 0.3 | 0.1 |
| 20 | 0.4 | 0.4 | 0.1 | 0.1 |
| 21 | 0.4 | 0.2 | 0.2 | 0.2 |
| 22 | 0.4 | 0.25 | 0.1 | 0.25 |
| 23 | 0.4 | 0.25 | 0.25 | 0.1 |
| 24 | 0.4 | 0.1 | 0.1 | 0.4 |
| 25 | 0.4 | 0.1 | 0.25 | 0.25 |
| 26 | 0.4 | 0.1 | 0.4 | 0.1 |

It is a further object of the present invention to provide lipid aggregate-cargo complexes suitable for the delivery of the cargo to the interior of a cultured cell or of a tissue to modulate or affect at least one biological function thereof. Cargo molecules suitable for use in the formation of the lipid aggregate-cargo complexes in accordance with the present invention include any biologically relevant molecular capable of forming a cationic complex with the described lipid aggregates under physiological conditions, and may include, by way of non-limiting example, nucleic acids (including DNA and RNA), proteins, peptides and other biologically relevant macromolecules.

In some embodiments, lipid aggregate-cargo complexes formed in accordance with the present disclosure include at least one, optionally more than one, cargo molecule contacted under conditions that allow the complexation thereof with a lipid aggregate comprising a first cationic lipid and at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein each of said first and second cationic lipids have the structure:

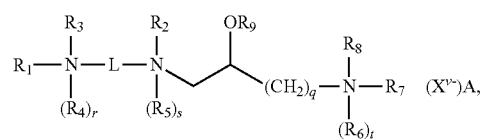

and salts thereof; where:

$R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is $-(CH_2)_q-N(R_6)_rR_7R_8$;

$R_3$ and $R_4$, independently, are hydrogens, $-(CH_2)_p-NH_2$, an alkyl, an or alkyl, or alkynyl groups optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

p and q are independently an integer ranging from 1 to 6, inclusive;

$X^v$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{-(CH_2)_k-Y-(CH_2)_m\}_p-$, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both $OR_{13}$ and $N(R_{13})_2$ groups.

The lipid aggregate-cargo complexes can include all the limitations set forth above and incorporated herein.

It is a further object of the present invention to provide lipid aggregate-nucleic acid complexes suitable for the delivery of a nucleic acid to the interior of a cultured cell or of a tissue to modulate or affect at least one biological function thereof. Nucleic acid molecules suitable for use in the formation of the lipid aggregate-cargo complexes in accordance with the present invention include any biologically relevant nucleic acid molecular capable of forming a cationic complex with the described lipid aggregates under physiological conditions, and may include, by way of non-limiting example, DNA and RNA. In some preferred though non-limiting embodiments, the nucleic acid molecules used in the formation of the lipid aggregate-nucleic acid complexes may be an RNA molecules, such as an RNAi molecule (including siRNA, miRNA, and the like), an mRNA molecule, or an RNA molecule having at least one, optionally more than one, at least two, optionally more than two, at least three, optionally more than three, at least four, optionally more than four, or at least five expressible sequences encoding at least one, two, three, four or five, protein(s) or a polypeptide(s).

In some embodiments, lipid aggregate-nucleic acid complexes formed in accordance with the present disclosure include at least one, optionally more than one, nucleic acid molecule contacted under conditions that allow the complexation thereof with a lipid aggregate comprising first cationic lipid and at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein each of said first and second cationic lipids have the structure:

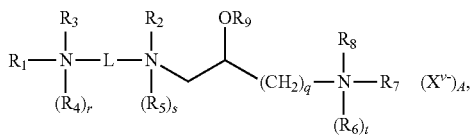

and salts thereof; where:

$R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is $-(CH_2)_q-N(R_6)_rR_7R_8$;

$R_3$ and $R_4$, independently, are hydrogens, $-(CH_2)_p-NH_2$, an alkyl, an alkenyl or alkynyl groups optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

p and q are independently an integer ranging from 1 to 6, inclusive;

$X^{v-}$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{-(CH_2)_k-Y-(CH_2)_m\}_p-$, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both $OR_{13}$ and $N(R_{13})_2$ groups.

The lipid aggregate-nucleic acid complexes can include all the limitations set forth above and incorporated herein.

The size of the nucleic acid molecules (e.g., the size thereof as measured in kilobases ("kb") suitable for complexation or incorporation in the lipid aggregate-nucleic acid complexes of the present invention can be any size between about 0.1 kB to about 20 kb. In some embodiments, the size of the nucleic acids used in the formation of the present lipid aggregate-nucleic acid complexes can be between about 0.4 kb to about 15 kb, about 0.5 kb to about 14 kb, between about 0.6 kb to about 13 kb, between about 0.7 kb to about 12 kb, between about 0.8 kb to about 11 kb, between about 0.1 kb to about 10 kb, between about 0.8 kb to about 9 kb, between about 0.9 kb to about 8 kb, between about 1 kb to about 7 kb, between about 1.5 kb to about 5 kb, between about 2 kb to about 4 kb, or any intervals falling therebetween.

In some embodiments, the size of the nucleic acids used in the formation of the present lipid aggregate-nucleic acid complexes can be from about 0.2 kb up to about 0.5 kb, up to about 1 kb, up to about 1.25 kb, up to about 1.5 kb, up to about 1.75 kb, up to about 2 kb, up to about 2.25 kb, up to about 2.5 kb, up to about 2.75 kb, up to about 3 kb, up to about 3.25 kb, up to about 3.5 kb, up to about 3.75 kb, up to about 4 kb, up to about 4.25 kb, up to about 4.5 kb, up to about 4.75 kb, up to about 5 kb, up to about 5.25 kb, up to about 5.5 kb, up to about 5.75 kb, up to about 6 kb, up to about 6.5 kb, up to about 7 kb, up to about 7.5 kb, up to about 8 kb, up to about 8.5 kb, up to about 9 kb, up to about 9.5 kb, up to about 10 kb, up to about 10.5 kb, up to about 11 kb, up to about 12 kb, up to about 13 kb, up to about 14 kb, or up to about 15 kb, up to about 20 kb, or any size therebetween.

In some further embodiments, the size of the RNA molecules (e.g., the size thereof as measured in kilobases ("kb") suitable for complexation or incorporation in the lipid aggregate-RNA complexes of the present invention as described above can be any size between about 0.1 kB to about 20 kb. In some embodiments, the size of the RNA molecules used in the formation of the present lipid aggregate-nucleic acid complexes can be between about 0.4 kb to about 15 kb, about 0.5 kb to about 14 kb, between about 0.6 kb to about 13 kb, between about 0.7 kb to about 12 kb, between about 0.8 kb to about 11 kb, between about 0.1 kb to about 10 kb, between about 0.8 kb to about 9 kb, between about 0.9 kb to about 8 kb, between about 1 kb to about 7 kb, between about 1.5 kb to about 5 kb, between about 2 kb to about 4 kb, or any intervals falling therebetween.

In some embodiments, the size of the RNA molecules used in the formation of the present lipid aggregate-nucleic acid complexes can be from about 0.2 kb up to about 0.5 kb, up to about 1 kb, up to about 1.25 kb, up to about 1.5 kb, up to about 1.75 kb, up to about 2 kb, up to about 2.25 kb, up to about 2.5 kb, up to about 2.75 kb, up to about 3 kb, up to about 3.25 kb, up to about 3.5 kb, up to about 3.75 kb, up to about 4 kb, up to about 4.25 kb, up to about 4.5 kb, up to about 4.75 kb, up to about 5 kb, up to about 5.25 kb, up to about 5.5 kb, up to about 5.75 kb, up to about 6 kb, up to about 6.5 kb, up to about 7 kb, up to about 7.5 kb, up to about 8 kb, up to about 8.5 kb, up to about 9 kb, up to about 9.5 kb, up to about 10 kb, up to about 10.5 kb, up to about 11 kb, up to about 12 kb, up to about 13 kb, up to about 14 kb, or up to about 15 kb, up to about 20 kb, or any size therebetween.

In some embodiments, the lipid aggregate-cargo, the lipid aggregate-nucleic acid or the lipid aggregate-RNA complexes formed in accordance with the presently described embodiments are stable for up to one hour, up to 4 hours, up to 10 hours, up to 24 hours, or up to any time period or interval therebetween.

It is a further object of the present invention to provide a method for transfecting a cultured cell or a tissue with a cargo molecule under conditions where the cargo molecule is introduced into the interior of the cultured cell or the tissue in order to modulate or affect at least one biological function thereof. Cargo molecules suitable for use in such methods include any biologically relevant cargo molecules capable of forming cationic lipid aggregate-cargo complexes under physiological conditions, and may include, by way of non-limiting example, nucleic acids (including DNA and RNA), proteins, peptides and other biologically relevant macromolecules.

In some embodiments, a method for transfecting a cultured cell or a tissue with a cargo molecule in accordance with the embodiments described herein may include obtaining a cargo molecule and forming a lipid aggregate-cargo complex by contacting the cargo molecule under conditions that allow the complexation thereof with a lipid aggregate comprising first cationic lipid and at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein each of said first and second cationic lipids have the structure:

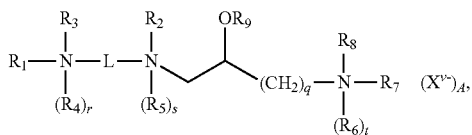

and salts thereof; where:

$R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is —$(CH_2)_q$—$N(R_6)_rR_7R_8$;

$R_3$ and $R_4$, independently, are hydrogens, —$(CH_2)_p$—$NH_2$, an alkyl, an alkenyl or alkynyl groups optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

p and q are independently an integer ranging from 1 to 6, inclusive;

$X^{v-}$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{-(CH_2)_k-Y-(CH_2)_m\}_p-$, where k and m, independently, are integers ranging from 1 to 10, inclusive, and p is an integer ranging from 1 to 6, inclusive, and Y is O, S, CO, COO, CONR$_{11}$, NR$_{11}$CO, or NR$_{11}$COR$_{11}$N where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, NR$_{12}$CO, NR$_{12}$COO, or NR$_{12}$CONR$_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more OR$_{13}$, CN, halogens, N(R$_{13}$)$_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both OR$_{13}$ and N(R$_{13}$)$_2$ groups, and contacting the lipid aggregate-cargo complex with a cultured cell or a tissue under conditions where the cargo molecule is transfected into the cell or tissue to modulate at least biological function thereof.

The lipid aggregate-cargo complexes used in the aforementioned method can include all the limitations set forth above and incorporated herein.

It is a further object still of the present invention to provide a method for transfecting a cultured cell or a tissue with a nucleic acid molecule under conditions where the nucleic acid molecule is introduced into the interior of the cultured cell or the tissue in order to modulate or affect at least one biological function thereof. Nucleic acid molecules suitable for use in the formation of the lipid aggregate-nucleic acid complexes in accordance with the present invention include any biologically relevant nucleic acid molecular capable of forming a cationic complex with the described lipid aggregates under physiological conditions, and may include, by way of non-limiting example, DNA and RNA. In some preferred though non-limiting embodiments, the nucleic acid molecules used in the formation of the lipid aggregate-nucleic acid complexes may be an RNA molecules, such as an RNAi molecule (including siRNA, miRNA, and the like), an mRNA molecule, or an RNA molecule having at least one, optionally more than one, at least two, optionally more than two, at least three, optionally more than three, at least four, optionally more than four, or at least five expressible sequences encoding at least one, two, three, four or five, protein(s) or a polypeptide(s).

In some embodiments, a method for transfecting a cultured cell or a tissue with a nucleic acid molecule in accordance with the embodiments described herein may include obtaining a nucleic acid molecule and forming a lipid aggregate-nucleic acid complex by contacting the nucleic acid molecule under conditions that allow the complexation thereof with a lipid aggregate comprising first cationic lipid and at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein each of said first and second cationic lipids have the structure:

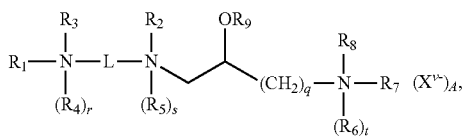

and salts thereof; where:

$R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is $-(CH_2)_q-N(R_6)_rR_7R_8$;

$R_3$ and $R_4$, independently, are hydrogens, $-(CH_2)_p-NH_2$, an alkyl, an alkenyl or alkynyl groups optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

p and q are independently an integer ranging from 1 to 6, inclusive;

$X^v$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{-(CH_2)_k-Y-(CH_2)_m\}_p-$, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both $OR_{13}$ and $N(R_{13})_2$ groups, and contacting the lipid aggregate-nucleic acid complex with a cultured cell or a tissue under conditions where the cargo molecule is transfected into the cell or tissue to modulate at least biological function thereof.

The lipid aggregate-nucleic acid complexes used in the aforementioned method can include all the limitations set forth above and incorporated herein.

Cell Reprogramming

The generation of human induced Pluripotent Stem (iPS) cells holds great promise for development of regenerative medicine therapies to treat a wide range of human diseases. The generation of human induced Pluripotent Stem (iPS) cells by retroviral expression of four reprogramming factors opened the potential for regenerative medicine therapies based on patient-specific, personalized stem cells (Takahashi and Yamanaka, 2006; Takahashi et al., 2007; Yu et al., 2007). However, the generation of iPS cells in the absence of integrative DNA vectors remains problematic and is a barrier to fully realizing the therapeutic potential for iPS cells. Several methods based on DNA, RNA, miRNAs and proteins have been developed to generate integration-free iPS cells, and the advantages and disadvantages have been discussed widely in the scientific literature. A variety of methods exist to introduce mRNA molecules encoding factors required for mRNA reprogramming (see, e.g., U.S. Pat. No. 8,716,465 granted to Rossi, et al). Recently, others have reported systems to reprogram somatic cells into iPS cells that involve introducing a single self-replicating VEE-RF RNA replicon that expresses four reprograming factors in a single construct (WO 2013/177133 by Dowdy and Yoshioka, and Yoshioka et al, Cell Stem Cell, 2014, both of which are hereby incorporated by reference in their entirety as though fully set forth herein). While these methods solve the problems of ensuring that the proper expression constructs are targeted to each transfected cell, the transfection reagents used are not ideal for RNA delivery, particularly for the large RNA constructs required for the delivery of at least four distinct coding regions and all the regulatory sequences required for proper expression and maintenance of the construct. There exists a need for transfection reagents, such as, e.g., lipid aggregate composition, that can efficiently introduce large (greater than 5 kB up to about 15 kb) RNA sequences to somatic cells for reprogramming applications.

Thus it is an object of the present invention to provide a lipid aggregate composition that can efficiently deliver large (>5 kb up to about 20 kb) RNA constructs to somatic cells for the reprogramming thereof into somatic cells and methods of using same for the purpose of reprograming somatic cells to induced pluripotent stem cells (hereinafter referred to as "iPS cells").

In an embodiment, a method for reprogramming a somatic cell into an iPS cell may include obtaining a cultured somatic cell and contacting the cultured somatic cell with a lipid aggregate-RNA complex where the RNA molecule encodes at least one but optionally up to 5 cellular reprogramming factors under conditions that permit the expression of the reprogramming factors. Any cultured somatic cell may be used in the practice of the present invention without limitation, and the identification of an appropriate cell lineage for reprogramming, and the conditions under which optimal reprogramming may be accomplished is well within the purview of one having ordinary skill level in the art. Exemplary somatic cells suitable for use with the present methods may include, though are not limited to, fibroblasts, myeloid cells, PBMCs, epithelial cells, neurons, glial cells, hepatocytes, and the like. In certain preferred though non-limiting embodiments, fibroblasts may be selected for use.

The lipid aggregates used in the production of the lipid aggregate-RNA complexes will include a first cationic lipid and at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein each of said first and second cationic lipids have the structure:

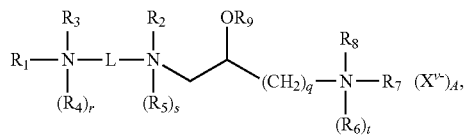

and salts thereof; where:

$R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is —$(CH_2)_q$—$N(R_6)_r R_7 R_8$;

$R_3$ and $R_4$, independently, are hydrogens, —$(CH_2)_p$—$NH_2$, an alkyl, an alkenyl or alkynyl groups optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

p and q are independently an integer ranging from 1 to 6, inclusive;

$X^v$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{-(CH_2)_k-Y-(CH_2)_m\}_p-$, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both $OR_{13}$ and $N(R_{13})_2$ groups, and contacting the lipid aggregate-nucleic acid complex with a cultured cell or a tissue under conditions where the cargo molecule is transfected into the cell or tissue to modulate at least biological function thereof.

The lipid aggregate-RNA complexes used in the aforementioned method can include all the limitations set forth above and incorporated herein.

In some embodiments, the RNA molecule used to for a complex with the lipid aggregates can be from about 4 kb, up to about 4.25 kb, up to about 4.5 kb, up to about 4.75 kb, up to about 5 kb, up to about 5.25 kb, up to about 5.5 kb, up to about 5.75 kb, up to about 6 kb, up to about 6.5 kb, up to about 7 kb, up to about 7.5 kb, up to about 8 kb, up to about 8.5 kb, up to about 9 kb, up to about 9.5 kb, up to about 10 kb, up to about 10.5 kb, up to about 11 kb, up to about 12 kb, up to about 13 kb, up to about 14 kb, or up to about 15 kb.

In some embodiments, the RNA molecule comprises at least one expressible sequence encoding a protein.

In some embodiments, the RNA construct includes one or more expressible sequences each encoding a protein required for cellular reprogramming. In some embodiments, the expressible sequence(s) found in the RNA molecule may encode OCT4. In some embodiments, the expressible sequence(s) found in the RNA molecule may encode KLF4. In some embodiments, the expressible sequence(s) found in the RNA molecule may encode SOX2. In some embodiments, the expressible sequence(s) found in the RNA molecule may encode c-MYC. In some embodiments, the expressible sequence(s) found in the RNA molecule may encode GLIS1.

In some embodiments, the RNA molecule may include up to four expressible sequences each encoding proteins required for cellular reprograming. For example, the RNA molecule may include four expressible sequences encode proteins selected from the list OCT4, KLF4, SOX2, c-MYC and GLIS1. In some embodiments, the RNA molecule comprises up to five expressible sequences each encoding proteins required for cellular reprograming, the five expressible sequences encoding, e.g., OCT4, KLF4, SOX2, c-MYC and GLIS1.

In some non-limiting embodiments, the RNA molecule used in accordance with the present invention may include a self-replicating Venezuelan Equine Encephalitis (VEE) replicon Direct Hepatocyte Reprogramming It is yet a further object of the present invention to provide a method for directly reprogramming a somatic cell into an induced hepatocyte as described in Simeonov, et al. PLoS One. 2014 Jun. 25; 9(6):e100134 and PCT Publication No. WO 2014039768, Huang et al Cell Stem Cell 14, 370-384, Mar. 6, 2014, and Du et al., Cell Stem Cell 14, 394-403, Mar. 6, 2014) all of which are hereby expressly incorporated by reference), said method not requiring that the somatic cell first be reprogrammed into an iPS cells.

In an embodiment, a method for reprogramming a somatic cell into an induced-hepatocyte (iHEP) cell may include obtaining a cultured somatic cell and contacting the cultured somatic cell with a lipid aggregate-RNA complex where the RNA molecule encodes at least one but optionally up to 5 cellular reprogramming factors under conditions that permit the expression of the reprogramming factors required for the reprogramming thereof to an iHEP cell. Any cultured somatic cell may be used in the practice of the present invention without limitation, and the identification of an appropriate cell lineage for reprogramming, and the conditions under which optimal reprogramming may be accomplished is well within the purview of one having ordinary skill level in the art. Exemplary somatic cells suitable for use with the present methods may include, though are not limited to, fibroblasts, myeloid cells, PBMCs, epithelial cells, neurons, glial cells, and the like. In certain preferred though non-limiting embodiments, fibroblasts may be selected for use.

The lipid aggregates used in the production of the lipid aggregate-RNA complexes will include a first cationic lipid and at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein each of said first and second cationic lipids have the structure:

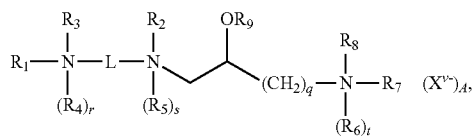

and salts thereof; where:

$R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is $-(CH_2)_q-N(R_6)_t R_7 R_8$;

$R_3$ and $R_4$, independently, are hydrogens, $-(CH_2)_p NH_2$, an alkyl, an alkenyl or alkynyl groups optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

p and q are independently an integer ranging from 1 to 6, inclusive;

$X^v$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{-(CH_2)_k-Y-(CH_2)_m\}_p-$, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both $OR_{13}$ and $N(R_{13})_2$ groups, and contacting the lipid aggregate-nucleic acid complex with a cultured cell or a tissue under conditions where the cargo molecule is transfected into the cell or tissue to modulate at least biological function thereof.

The lipid aggregate-RNA complexes used in the aforementioned method can include all the limitations set forth above and incorporated herein.

In some embodiments, the RNA construct includes one or more expressible sequences each encoding a protein required for direct cellular reprograming of a somatic cell to an iHEP. In some embodiments, the expressible sequence(s) found in the RNA molecule may encode HNF1A. In some embodiments, the expressible sequence(s) found in the RNA molecule may encode FOXA1. In some embodiments, the expressible sequence(s) found in the RNA molecule may encode FOXA3. In some embodiments, the expressible sequence(s) found in the RNA molecule may encode HNF4A. In some embodiments, the expressible sequence(s) found in the RNA molecule may encode HNF1A. In some embodiments, the one or more RNA molecules comprise expressible sequences encoding the protein HNF1A and at two proteins selected from the list FOXA1, FOXA3, and HNF4A.

The transfected cells may be maintained under conditions that are permissive to the reprogramming thereof into an iHEP cell.

Genome Editing

Genome engineering is rapidly becoming the methodology of choice for studying basic biological functions and it holds tremendous promise in the fields of therapeutics, cell engineering and regenerative medicine. Genome engineering allows specific, guided and efficient introduction of mutations into the germline genome of cultured cells to modulate the function thereof. Several systems for genome engineering are known in the art and include, e.g., sequence-specific zinc fingers (ZF), transcription activator-like effector (TALE) protein systems fused to a nuclease, or more recently, the highly efficient clustered, regularly interspaced short palindromic repeat (CRISPR) system in which a guide RNA (gRNA) targets a nuclease or a modified nuclease (e.g., Cas9 or a variant thereof) to a specific genetic locus to facilitate sequence-specific genomic modification (disclosed in, e.g., U.S. Pat. Nos. 8,771,945 and 8,697,359 to Zhang, U.S. Patent Appl. Publ. No. 2014/0179006 by Zhang, and U.S. Patent Appl. Publ No 201/0193915 by Lamb et al, all of which are hereby incorporated by reference). Adapting these systems to an RNA based delivery system using a transfection system with improved transfection efficiency, particularly in therapeutically important cells, such as, stem cells, neurons, hepatocytes, can improve the likelihood of successful targeting events.

Thus, it is yet a further object of the present invention to provide a lipid aggregate transfection reagent that achieves at least 2-fold, at least 2.5-fold, at least 3-fold, and least 3.5-fold, at least 4-fold, at least 4.5-fold, at least 5-fold, or greater than 5-fold improved genome editing efficiency than currently available systems.

In some embodiments, a method for expressing a protein involved in genome editing in a cell may include obtaining a cultured cell and contacting the cultured cell with a lipid aggregate-RNA complex where the RNA molecule includes at least one sequence required for genome editing, and maintaining the cultured cell in the presence of the lipid aggregate-RNA complex under conditions that permit the expression of the genome editing protein in the cell. Any cultured cell may be used in the practice of the present invention without limitation, and the identification of an appropriate cell lineage for genome editing, and the conditions under which optimal genome editing may be accomplished is well within the purview of one having ordinary skill level in the art. Exemplary somatic cells suitable for use with the present methods may include, though are not limited to, fibroblasts, embryonic stem cells iPS cells, embryonic cell-derived pluripotent or multipotent cell lines, myeloid cells, PBMCs, epithelial cells, neurons, glial cells, hepatocytes, and the like. In certain preferred though non-limiting embodiments, iPS cells or other stem cells may be selected for use.

The lipid aggregates used in the production of the lipid aggregate-RNA complexes will include a first cationic lipid and at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein each of said first and second cationic lipids have the structure:

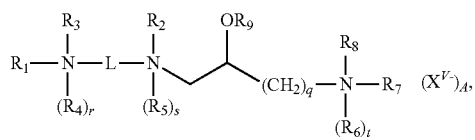

and salts thereof; where:

$R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is $-(CH_2)_q-N(R_6)_rR_7R_8$;

$R_3$ and $R_4$, independently, are hydrogens, $-(CH_2)_p-NH_2$, an alkyl, an alkenyl or alkynyl groups optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

p and q are independently an integer ranging from 1 to 6, inclusive;

$X^{v-}$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{-(CH_2)_k-Y-(CH_2)_m\}_p-$, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$ is hydrogen or an alkyl, alkenyl or alkynyl group, and wherein at least one of $R_3$ and $R_4$, when present as alkyl groups, are substituted with both $OR_{13}$ and $N(R_{13})_2$ groups, and contacting the lipid aggregate-nucleic acid complex with a cultured cell or a tissue under conditions where the cargo molecule is transfected into the cell or tissue to modulate at least one biological function thereof.

The lipid aggregate-RNA complexes used in the aforementioned method can include all the limitations set forth above and incorporated herein.

In some embodiments of the present invention, the RNA molecule comprises an expressible sequence encoding a CRISPR protein. In some embodiments, the RNA molecule comprises an expressible sequence encoding a Cas protein. In some embodiments, the RNA molecule comprises an expressible sequence encoding a Cas9 protein or a Cas2 protein. In some embodiments, the RNA molecule comprises at least one guide RNA (gRNA) sequence used for targeting at least one CRISPR protein to a specific genomic locus. In some embodiments, the RNA molecule comprises an expressible sequence encoding a TAL-effector protein.

In some embodiments of the present invention, the cell contacted with the lipid aggregate-RNA complex may be a somatic cell, an iPS cell, and embryonic stem cell, a fibroblast, a lymphoid cell, a neuron, a cell line, a transformed cell or a difficult to transfect cell.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The following Examples are provided to illustrate certain aspects of the disclosure and to aid those of skill in the art in practicing the disclosure. These Examples are in no way to be considered to limit the scope of the disclosure in any manner.

Example 1

Expression of GFP in H9 ESCs

H9-derived human neural stem cells (H9-hNSCs) (Gibco® Life Technologies) were maintained and propagated on Geltrex® as an adherent culture in complete StemPro® NSC SFM on 24-well plates according to manufacturer's instructions. Cells were plated so as to achieve 70-90% confluence on the day of transfection. mRNA containing a GFP coding region was prepared from an expression vector containing an in-frame GFP expression construct under the control of T7 promoter using the Ambion® mMESSAGE mMACHINE® T7 Ultra Kit (Life Technologies) according to manufacturer instructions. The amount of GFP mRNA prepared was quantitated.

Complexation of the prepared GFP mRNA with lipid aggregates was performed as follows: For each well of cells to be transfected, 1.5 µl of lipid aggregate Formulation #21 or 1.5 µl of Lipofectamine® 2000 (LF2K, Life Technologies) were diluted in Opti-MEM® Medium (Gibco® Life Technologies). The diluted lipid preparations were mixed well and left at ambient temperature for several minutes. For each well of cells to be transfected, 0.5 to 1 µg of the prepared GFP mRNA was diluted in 25 µl Opti-MEM® Medium and mixed well. 25 µl of the diluted GFP mRNA was added to each of the diluted lipid aggregate preparations (i.e., either the Formulation 21 or Lipofectamine® 2000) at a 1:1 ratio, mixed well, and the resulting mRNA-lipid aggregate complexes were incubated at ambient temperature for approximately 5 minutes.

For each well of cells, 50 µl of the mRNA-lipid aggregate complex was added to the cultured H9-hNSCs, and the cultures were maintained for 24-48 hrs. in the presence of the mRNA-lipid aggregate complexes. Cells were harvested and GFP expression quantitated and normalized. The results are depicted in FIG. 1, which clearly demonstrates superior transfection efficiency of the lipid aggregates described herein when compared to a commercially available transfection reagent.

Example 2

Improved Cleavage Efficiency of CRISPR Nucleases in iPS Cells iPS cells were prepared according to protocols known in the art and seeded in a Geltrex®-Matrix coated 12-well culture dish. Transfection was performed in iPSCs with 3 ul of Lipofectamine® 2000 or 3u1 of Lipofectamine® 3000 as indicated and according to manufacturer's instructions, to deliver a GeneArt® CRISPR Nuclease vector targeting the HPRT locus. Transfection was also performed with GeneArt® CRISPR Nuclease RNA editing system targeting the HPRT locus and 3u1 of Formulation 21 lipid aggregate complex. RNA editing system utilizes a Cas9 mRNA, which was prepared via in vitro transcription with the Ambion® mMESSAGE mMACHINE® Kit, and a gRNA which was transcribed using the Ambion® MEGAshortscript™ Kit. Cells were harvested 72-hours post-transfection and cleavage efficiency was determined using the GeneArt® Genomic Cleavage Detection Kit.

Figure 2A:
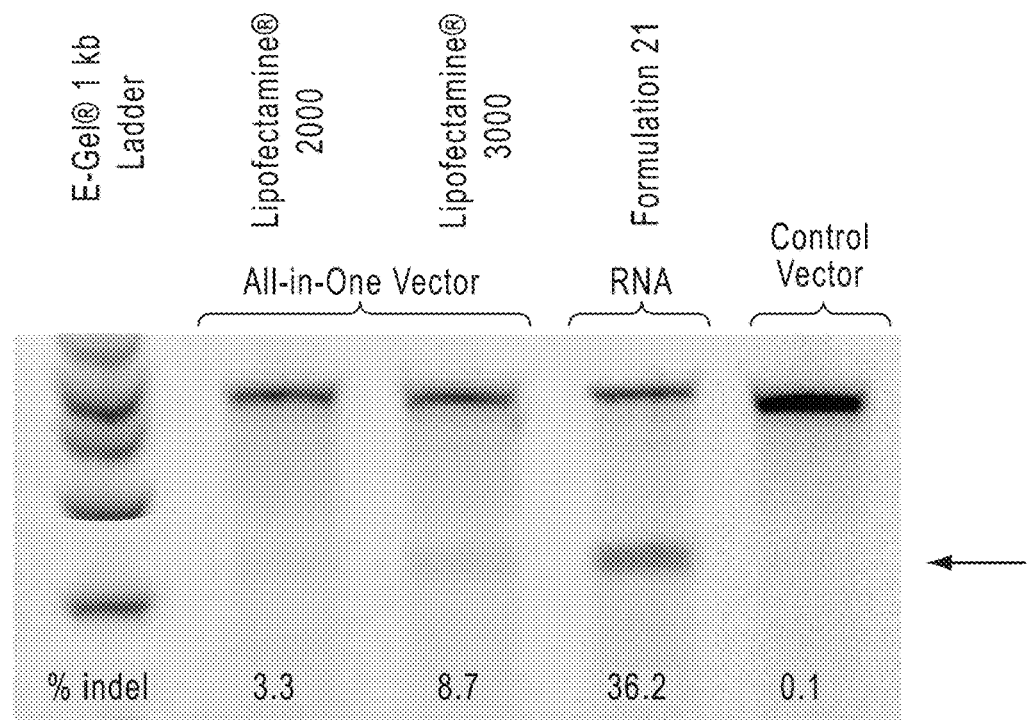
FIG. 2A and FIG. 2B shows results using an mRNA based form of Cas9 with a guide-RNA for gene editing with the lipid aggregates described herein when compared with a DNA-based gene editing system using Lipofectamine® 2000.
Figure 2B:
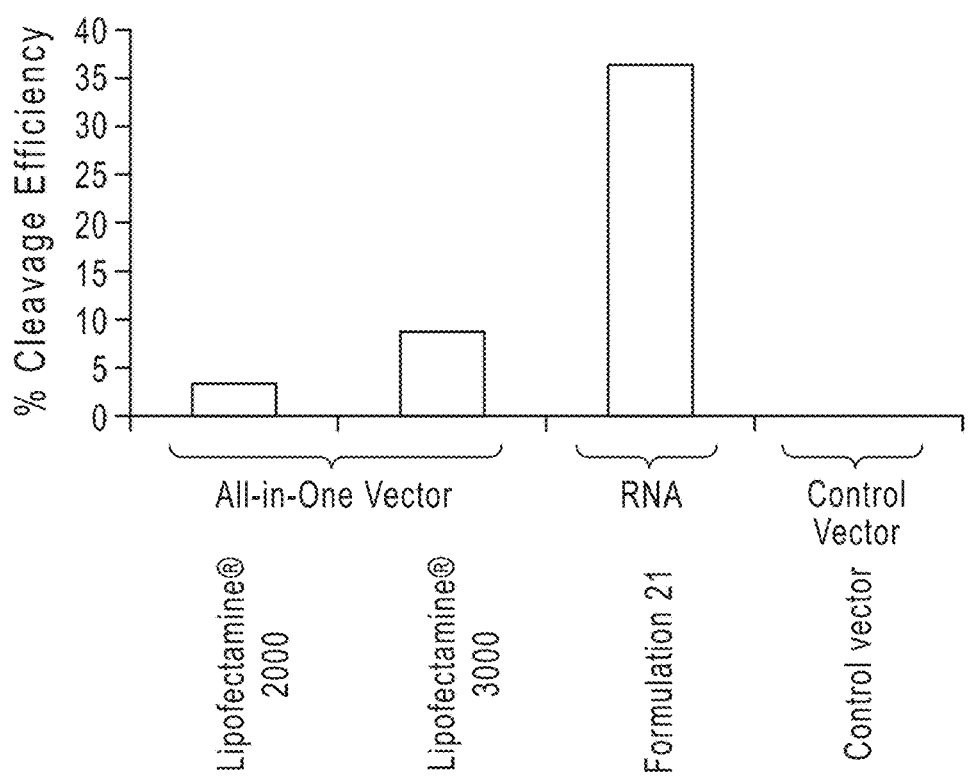

Results are shown in FIG. 2A-B, which clearly demonstrate that using an mRNA based form of Cas9 with a guide-RNA for gene editing with the lipid aggregates described herein for transfection results in at least 4-fold more targeted cleavage of the host cell genome when compared to standard DNA based editing approaches.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A lipid aggregate comprising a first cationic lipid (i) dihydroxyl-dimyristylspermine (DHDMS) or salt thereof or (ii) hydroxyl-dimyristylspermine (HDMS) or salt thereof, at least a second cationic lipid, a first neutral lipid and optionally a second neutral lipid, wherein said lipid aggregate is suitable for forming a cationic complex with a nucleic acid under aqueous conditions, wherein said first and second cationic lipids are different from each other, and wherein said DHDMS has the structure:

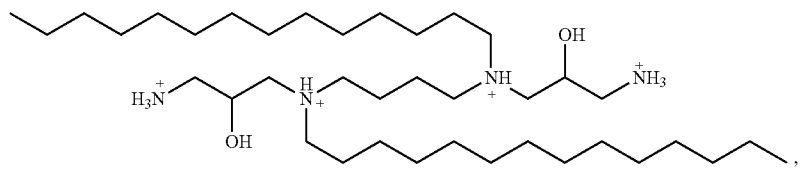

and salts thereof,
and said HDMS has the structure:

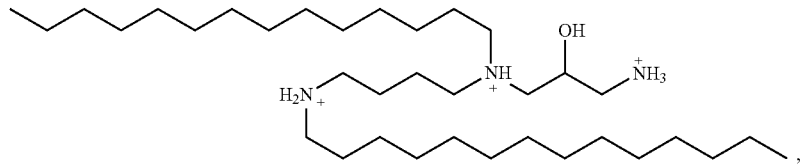 [SMILES: CCCCCCCCCCCCCCNCCCCN(CCCCCCCCCCCCCC)CC(O)CN]

and salts thereof.

2. The lipid aggregate of claim 1, comprising a cationic lipid selected from the list consisting of TMTPS, DOGS, DPPES, DOTMA, DOTAP, DDAB, DMRIE, DOSPA, and DOSPER.

3. The lipid aggregate of claim 1, wherein said first cationic lipid is DHDMS.

4. The lipid aggregate of claim 1, wherein said first cationic lipid is HDMS.

5. The lipid aggregate of claim 1, wherein said first cationic lipid is DHDMS and the second cationic lipid is HDMS and further comprising an additional cationic lipid is selected from the list consisting of TMTPS, DOGS, DPPES, DOTMA, DOTAP, DDAB, DMRIE, DOSPA, and DOSPER.

6. The lipid aggregate of claim 3, wherein the molar ratio of DHDMS is from about 0.1 to about 0.4.

7. The lipid aggregate of claim 4, wherein the molar ratio of HDMS is from about 0.1 to about 0.4.

8. The lipid aggregate of claim 1, wherein the neutral lipid is selected from the group consisting of DOPE, DOPC and cholesterol.

9. The lipid aggregate of claim 1, wherein said second neutral lipid selected from the group consisting of DOPE, DOPC and cholesterol, wherein said second neutral lipid is different from said first neutral lipid.

10. The lipid aggregate of claim 1, wherein said first neutral lipid is cholesterol.

11. The lipid aggregate of claim 1, wherein said second neutral lipid is DOPE.

12. The lipid aggregate of claim 10, wherein the molar ratio of cholesterol is about 0.1 to about 0.4.

13. The lipid aggregate of claim 11, wherein the molar ratio of DOPE is about 0.1 to about 0.4.

14. The lipid aggregate of claim 1, wherein the first neutral lipid is cholesterol and the second neutral lipid is DOPE.

15. The lipid aggregate of claim 14, wherein the molar ratio of each of cholesterol and DOPE is about 0.1 to about 0.4.

16. A lipid aggregate-nucleic acid complex comprising the lipid aggregate of claim 1 contacted with a nucleic acid molecule.

17. A lipid aggregate-nucleic acid complex comprising the lipid aggregate of claim 1 contacted with an RNA molecule.

18. The lipid aggregate-nucleic acid complex of claim 17, wherein the RNA molecule comprises at least one expressible sequence encoding a protein.

19. A lipid aggregate-nucleic acid complex comprising the lipid aggregate of claim 1 contacted with an mRNA molecule.

20. The lipid aggregate-nucleic acid complex according to claim 16, wherein the lipid aggregate-nucleic acid complex is stable for up to 1 hour.

21. The lipid aggregate-nucleic acid complex according to claim 16, wherein the lipid aggregate-nucleic acid complex is stable for up to 4 hours.

22. The lipid aggregate-nucleic acid complex according to claim 16, wherein the lipid aggregate-nucleic acid complex is stable for up to 10 hours.

23. The lipid aggregate-nucleic acid complex according to claim 16, wherein the lipid aggregate-nucleic acid complex is stable for up to 24 hours.

24. A method of transfecting a cell with an RNA molecule, the method comprising:
obtaining a lipid aggregate according to claim 1;
contacting said lipid aggregate with an RNA molecule to form a lipid aggregate-RNA complex; and
contacting the lipid-aggregate-RNA with a cell or a tissue under conditions where the RNA molecule is transfected to the interior of the cell.

25. The method of claim 24, wherein said RNA molecule is an mRNA molecule.

26. The method of claim 24, wherein said RNA molecule comprises an expressible sequence encoding at least one protein.

27. The method of claim 24, wherein said RNA molecule comprises an expressible sequence encoding at least two proteins.

28. The method of claim 24, wherein said RNA molecule comprises an expressible sequence encoding at least 3 proteins.

29. The method of claim 24, wherein said RNA molecule comprises an expressible sequence encoding four proteins.

30. The method of claim 24, wherein said RNA molecule comprises an expressible sequence encoding at least five proteins.

31. The method of claim 24, wherein said RNA molecule is between about 0.4 kb to about 15 kb.

32. The method of claim 24, wherein said RNA molecule is between about 0.5 kb to about 14 kb.

33. The method of claim 24, wherein said RNA molecule is between about 0.6 kb to about 13 kb.

34. The method of claim 24, wherein said RNA molecule is between about 0.7 kb to about 12 kb.

35. The method of claim 24, wherein said RNA molecule is between about 0.8 kb to about 11 kb.

36. The method of claim 24, wherein said RNA molecule is between about 0.1 kb to about 10 kb.

37. The method of claim 24, wherein said RNA molecule is between about 0.8 kb to about 9 kb.

38. The method of claim 24, wherein said RNA molecule is between about 0.9 kb to about 8 kb.

39. The method of claim 24, wherein said RNA molecule is between about 1 kb to about 7 kb.

40. The method of claim 24, wherein said RNA molecule is between about 1.5 kb to about 5 kb.

41. The method of claim 24, wherein said RNA molecule is between about 2 kb to about 4 kb.

42. The method of claim 24, wherein said RNA molecule is from about 0.2 kb up to about 0.5 kb, up to about 1 kb, up to about 1.25 kb, up to about 1.5 kb, up to about 1.75 kb, up to about 2 kb, up to about 2.25 kb, up to about 2.5 kb, up to about 2.75 kb, up to about 3 kb, up to about 3.25 kb, up to about 3.5 kb, up to about 3.75 kb, up to about 4 kb, up to about 4.25 kb, up to about 4.5 kb, up to about 4.75 kb, up to about 5 kb, up to about 5.25 kb, up to about 5.5 kb, up to about 5.75 kb, up to about 6 kb, up to about 6.5 kb, up to about 7 kb, up to about 7.5 kb, up to about 8 kb, up to about 8.5 kb, up to about 9 kb, up to about 9.5 kb, up to about 10 kb, up to about 10.5 kb, up to about 11 kb, up to about 12 kb, up to about 13 kb, up to about 14 kb, or up to about 15 kb.

43. The method of claim 24, wherein said RNA molecule comprises a self-replicating Venezuelan Equine Encephalitis (VEE) replicon.

* * * * *